US012773092B2

(12) United States Patent
Mizutani et al.

(10) Patent No.: US 12,773,092 B2
(45) Date of Patent: Oct. 27, 2026

(54) ENDOSCOPE SYSTEM, CONTROL METHOD, AND RECORDING MEDIUM

(71) Applicant: OLYMPUS CORPORATION, Tokyo (JP)

(72) Inventors: Chiharu Mizutani, Tokyo (JP); Hiroyuki Takayama, Tokyo (JP); Mingxuan Dai, Tokyo (JP); Masaru Yanagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 83 days.

(21) Appl. No.: 18/986,660

(22) Filed: Dec. 18, 2024

(65) Prior Publication Data

US 2025/0113977 A1 Apr. 10, 2025

Related U.S. Application Data

(63) Continuation of application No. PCT/JP2023/024350, filed on Jun. 30, 2023.

(60) Provisional application No. 63/359,269, filed on Jul. 8, 2022.

(51) Int. Cl.
*A61B 1/00* (2006.01)

(52) U.S. Cl.
CPC ...... *A61B 1/00006* (2013.01); *A61B 1/00039* (2013.01)

(58) Field of Classification Search
CPC ............ A61B 1/00006; A61B 1/00039; A61B 1/000096
See application file for complete search history.

(56) References Cited

U.S. PATENT DOCUMENTS

2014/0163359 A1 6/2014 Sholev et al.
2014/0228632 A1 8/2014 Sholev et al.
2015/0238276 A1 8/2015 Atarot et al.
2015/0332196 A1* 11/2015 Stiller .............. G06Q 10/06316 705/2

(Continued)

FOREIGN PATENT DOCUMENTS

WO 2013027201 A2 2/2013
WO 2014049598 A1 4/2014

(Continued)

OTHER PUBLICATIONS

International Search Report dated Aug. 15, 2023 received in PCT/JP2023/024350.

*Primary Examiner* — Timothy J Neal
(74) *Attorney, Agent, or Firm* — Scully, Scott, Murphy & Presser, P.C.

(57) ABSTRACT

An endoscope system for controlling a field of view of an endoscope on a basis of a control parameter, the endoscope system including: a storage configured to store history data on the control parameter during a surgery in association with subsidiary information on the surgery, the subsidiary information including information related to at least one of a surgeon, an operative method, or a patient of the surgery; and one or more processors including hardware, wherein the one or more processors are configured to calculate a recommended value of the control parameter on a basis of the history data, and wherein the history data is an operation log of a user interface for changing the control parameter.

16 Claims, 18 Drawing Sheets

(56) References Cited

U.S. PATENT DOCUMENTS

| | | | | |
|---|---|---|---|---|
| 2017/0035514 | A1* | 2/2017 | Fox | G06Q 10/10 |
| 2017/0172382 | A1 | 6/2017 | Nir et al. | |
| 2017/0212723 | A1 | 7/2017 | Atarot et al. | |
| 2018/0325604 | A1 | 11/2018 | Atarot et al. | |
| 2020/0397515 | A1 | 12/2020 | Frimer et al. | |
| 2021/0141597 | A1 | 5/2021 | Atarot et al. | |
| 2021/0169576 | A1* | 6/2021 | Yoshinaka | G06N 20/00 |
| 2022/0394161 | A1 | 12/2022 | Nir et al. | |
| 2022/0395159 | A1 | 12/2022 | Atarot et al. | |
| 2023/0123443 | A1 | 4/2023 | Atarot et al. | |
| 2023/0172675 | A1 | 6/2023 | Ogimoto et al. | |
| 2023/0180995 | A1 | 6/2023 | Takayama et al. | |
| 2023/0180996 | A1 | 6/2023 | Dai et al. | |
| 2023/0180998 | A1 | 6/2023 | Mizutani et al. | |

FOREIGN PATENT DOCUMENTS

| | | | |
|---|---|---|---|
| WO | 2015151098 | A2 | 10/2015 |
| WO | 2022054882 | A1 | 3/2022 |

* cited by examiner

ENDOSCOPE SYSTEM, CONTROL METHOD, AND RECORDING MEDIUM

CROSS-REFERENCE TO RELATED APPLICATIONS

This is a continuation of International Application PCT/JP2023/024350, with an international filing date of Jun. 30, 2023, which is hereby incorporated by reference herein in its entirety.

This application claims the benefit of U.S. Provisional Application No. 63/359,269, filed on Jul. 8, 2022, which is hereby incorporated by reference herein in its entirety.

TECHNICAL FIELD

The present disclosure relates to an endoscope system, a control method, and a control program.

BACKGROUND

Conventionally, an endoscope system that causes an endoscope to automatically follow a surgical instrument has been known (see PTL 1, for example). In laparoscopic surgery, it is important to maintain an appropriate field of view of an endoscope. According to PTL 1, the field of view of the endoscope is controlled such that the surgical instrument is arranged at a predetermined target point within an endoscope image, thereby maintaining an appropriate field of view.

SUMMARY

An aspect of the present disclosure is an endoscope system for controlling a field of view of an endoscope on a basis of a control parameter, the endoscope system including: a storage configured to store history data on the control parameter during a surgery in association with subsidiary information on the surgery, the subsidiary information including information related to at least one of a surgeon, an operative method, or a patient of the surgery; and one or more processors including hardware, wherein the one or more processors are configured to calculate a recommended value of the control parameter on a basis of the history data, and wherein the history data is an operation log of a user interface for changing the control parameter.

Another aspect of the present disclosure is a control method for controlling a field of view of an endoscope on a basis of a control parameter, the control method including: causing a storage to store history data on the control parameter during a surgery in association with subsidiary information on the surgery, the subsidiary information including information related to at least one of a surgeon, an operative method, or a patient of the surgery; and calculating a recommended value of the control parameter on a basis of the history data, wherein the history data is an operation log of a user interface for changing the control parameter.

Another aspect of the present disclosure is a non-transitory computer-readable recording medium storing a control program for causing a computer to execute a control method for controlling a field of view of an endoscope on a basis of a control parameter, the control method including: causing a storage to store history data on the control parameter during a surgery in association with subsidiary information on the surgery, the subsidiary information including information related to at least one of a surgeon, an operative method, or a patient of the surgery; and calculating a recommended value of the control parameter on a basis of the history data, wherein the history data is an operation log of a user interface for changing the control parameter.

DESCRIPTION OF EMBODIMENTS

First Embodiment

An endoscope system, a control method, and a control program according to a first embodiment of the present disclosure will be described with reference to the drawings.

Figure 1:
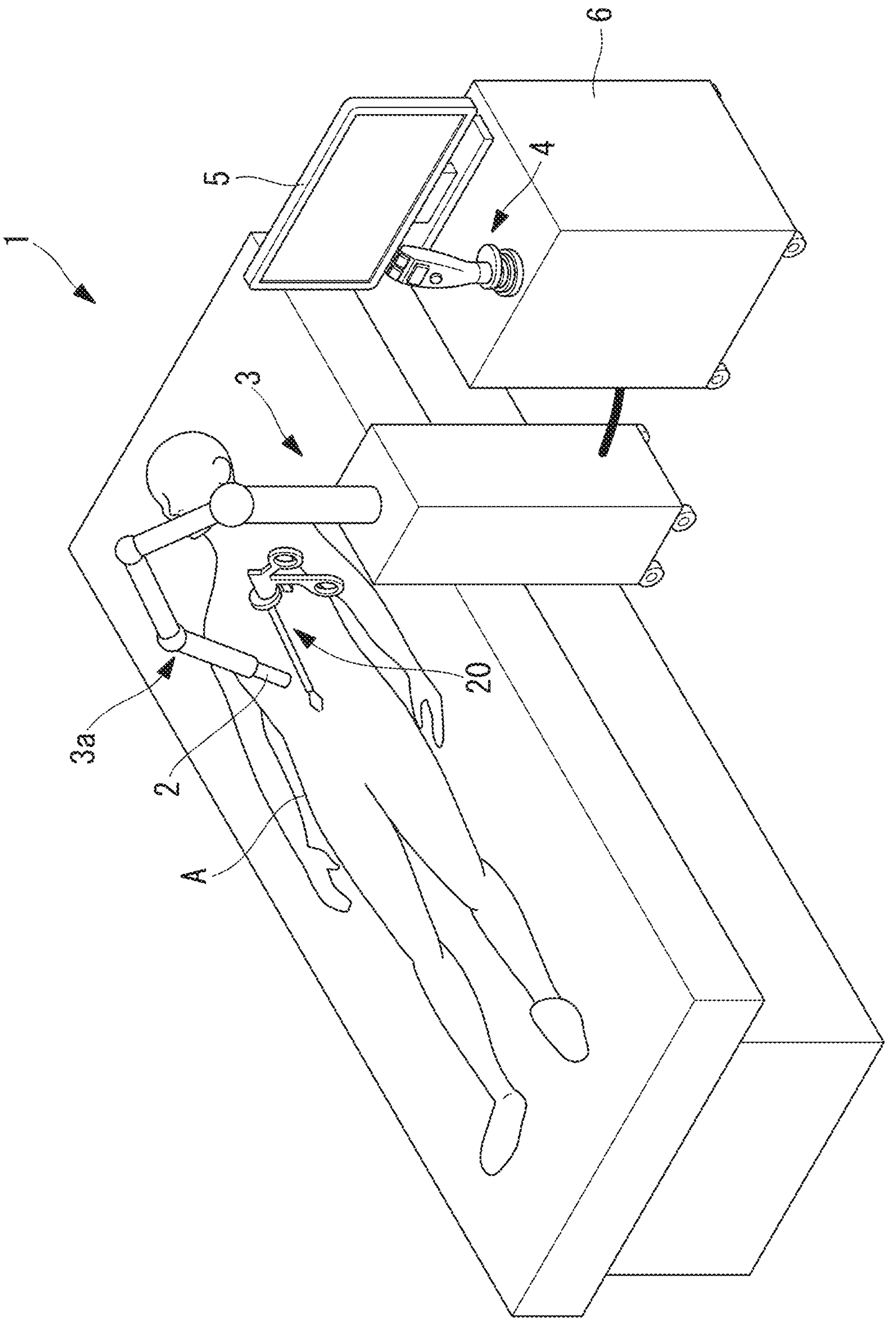
FIG. 1 is an overall configuration diagram of an endoscope system according to a first embodiment.

As illustrated in FIG. 1, an endoscope system 1 according to the present embodiment is used for a surgery of inserting an endoscope 2 and a surgical instrument 20 into the body of a patient who is a subject A and treating a treatment target site with the surgical instrument 20 while monitoring the surgical instrument 20 with the endoscope 2, and is used for a laparoscopic surgery, for example.

Figure 2:
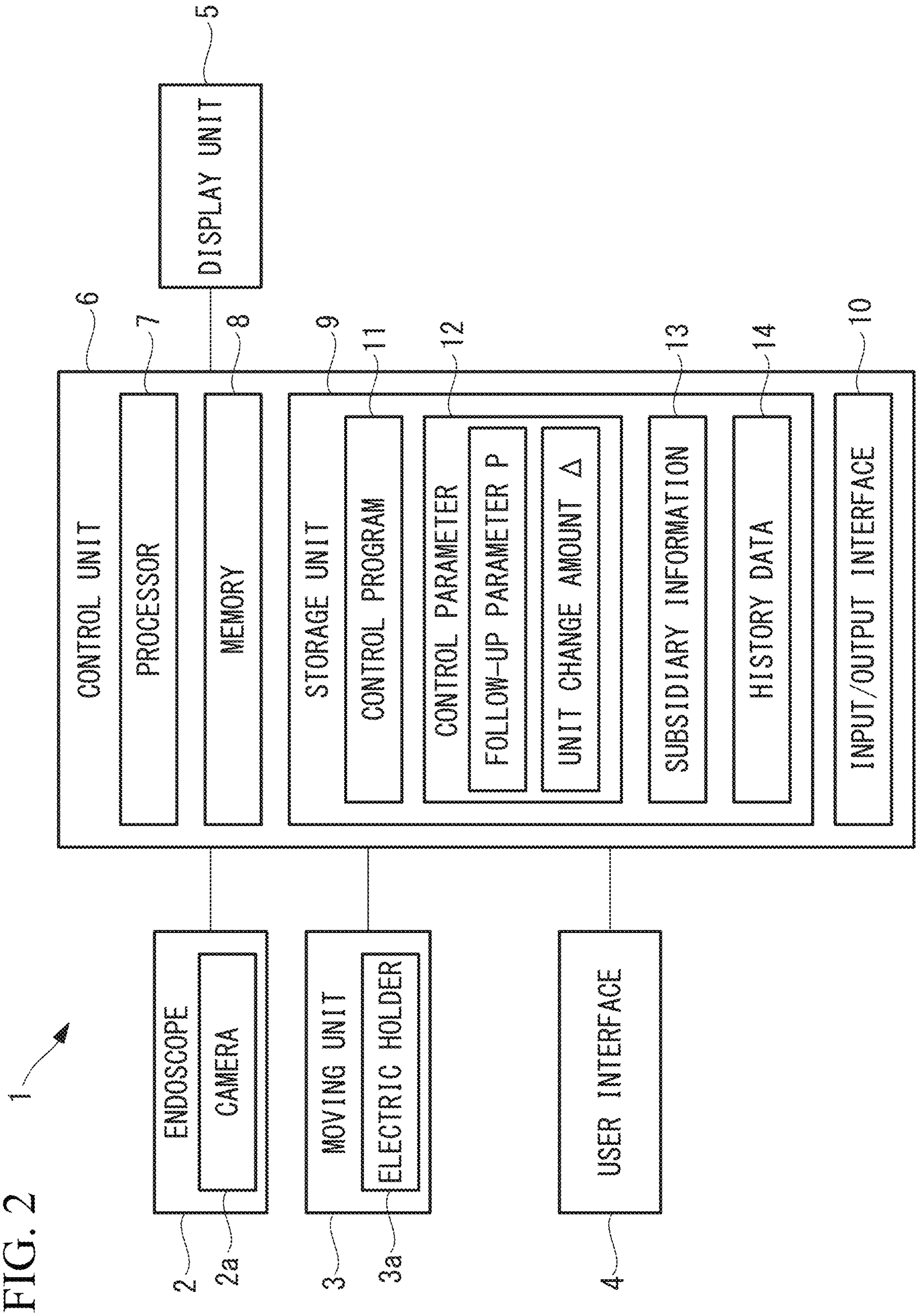
FIG. 2 is a block diagram of the endoscope system in FIG. 1.

As illustrated in FIGS. 1 and 2, the endoscope system 1 includes the endoscope 2, a moving unit 3 that changes the position and orientation of the endoscope 2, a user interface 4, a display unit 5, and a control unit 6.

The endoscope 2 has a camera 2*a* including an imaging element such as a CCD image sensor or a CMOS image sensor and acquires an image B in the subject A with the camera 2*a*. The camera 2*a* may be a three-dimensional camera that acquires a stereo image.

The image B is transmitted from the endoscope 2 to the display unit 5 by way of the control unit 6 and is displayed on the display unit 5. The display unit 5 is any display such as a liquid crystal display or an organic EL display.

The moving unit 3 includes an electric holder 3*a* composed of an articulated robot arm and is controlled by the control unit 6. The endoscope 2 is held at a tip of the electric holder 3*a*, and the position and orientation of a tip of the endoscope 2 are changed three-dimensionally by a movement of the electric holder 3*a*.

The moving unit 3 does not necessarily need to be separate from the endoscope 2 and may be formed integrally as part of the endoscope 2. Alternatively, the moving unit 3 may be another mechanism that can change the position and orientation of the tip of the endoscope 2, such as a bendable portion provided in the tip portion of the endoscope 2.

The user interface 4 includes an input device and accepts an input operation of the control unit 6 through the input device. The user interface 4 includes, for example, a voice user interface (VUI) having a microphone-equipped headset or the like and a graphical user interface (GUI) having a keyboard, a mouse, and a touch pad or the like. A user such as a surgeon can perform input to the control unit 6 by an operation of the GUI before and after a surgery and by an operation of the VUI during a surgery, for example.

The control unit 6 is an endoscope processor that controls the endoscope 2 and the moving unit 3. As illustrated in FIG. 2, the control unit 6 includes at least one processor 7, a memory 8, a storage unit 9, and an input/output interface 10.

The control unit 6 is connected to the peripheral equipment 2, 3, 4, and 5 by way of the input/output interface 10 and transmits/receives the image B and a signal or the like by way of the input/output interface 10.

The storage unit 9 is a computer-readable non-transitory recording medium and is a hard disk drive, an optical disk, a flash memory, or the like, for example. The storage unit 9 stores a control program 11 that causes the processor 7 to execute a control method which will be described later. The storage unit 9 also stores a control parameter 12 to be used for controlling the moving unit 3 and the subsidiary information 13 related to surgeries performed previously. The storage unit 9 also stores history data 14 on the control parameter 12 at least during a surgery.

Part of processing which will be described later to be executed by the processor 7 may be implemented by a dedicated logic circuit such as an FPGA (Field Programmable Gate Array), an SoC (System-On-A-Chip), an ASIC (Application Specific Integrated Circuit), or a PLD (Programmable Logic Device), or hardware or the like.

The processor 7 controls the moving unit 3 in accordance with the control program 11 read from the storage unit 9 into the memory 8 such as a RAM (Random Access Memory), thereby controlling a field of view F of the endoscope 2. Control over the field of view F of the endoscope 2 is follow-up control of causing the endoscope 2 to follow a follow-up target to continue capturing the follow-up target within the field of view F. The follow-up target is any object present in the image B during a surgery and is, for example, the predetermined surgical instrument 20, a predetermined organ, or a predetermined tissue.

Figure 3A:
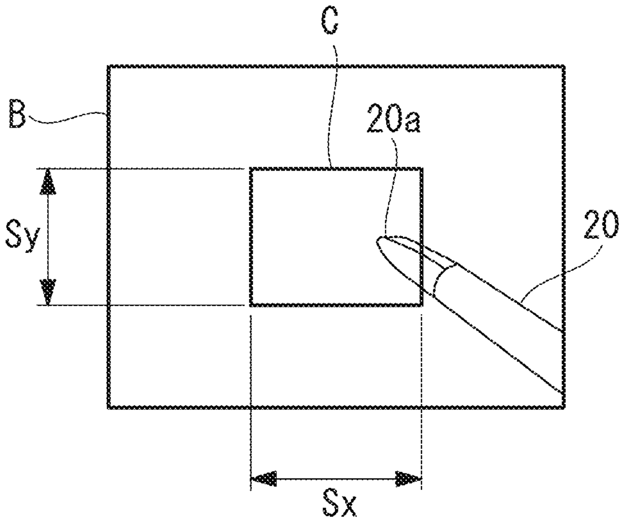
FIG. 3A is a diagram describing a follow-up parameter.
Figure 3B:
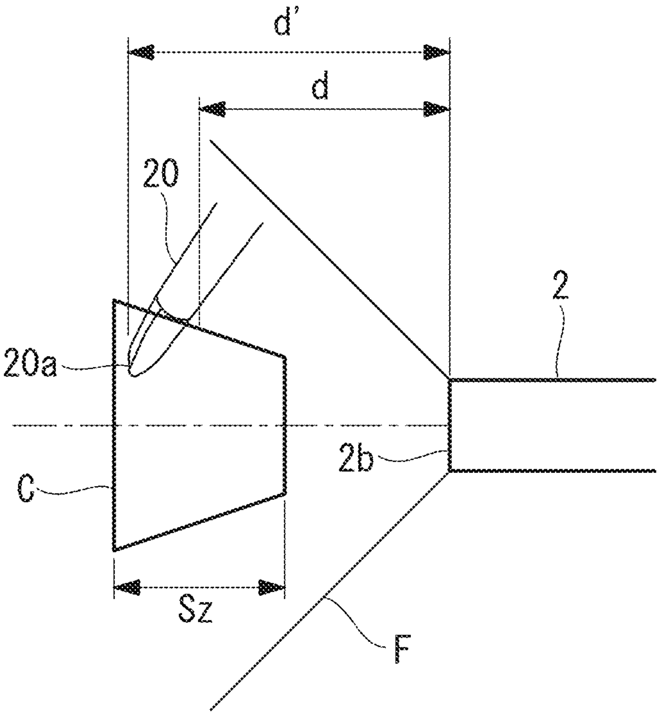
FIG. 3B is a diagram describing the follow-up parameter.
Figure 3C:
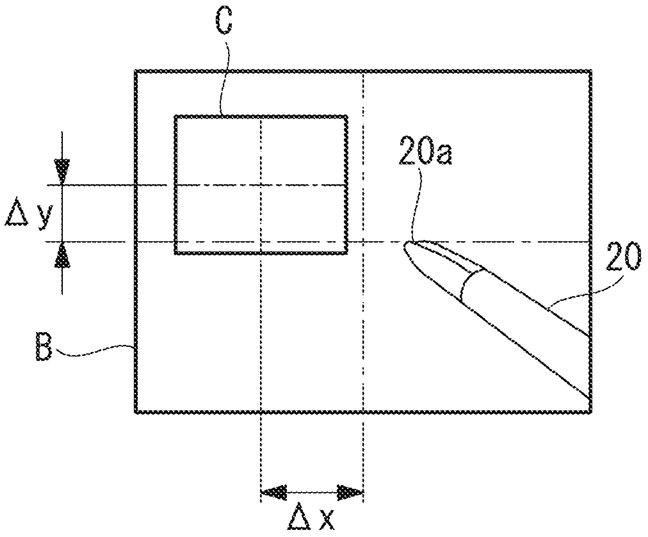
FIG. 3C is a diagram describing the follow-up parameter.

FIGS. 3A to 3C describe an example of the follow-up control in a case where the follow-up target is the surgical instrument 20. In this follow-up control, the processor 7 detects a three-dimensional position of a tip 20*a* of the surgical instrument 20 using a publicly-known means such as stereo measurement through use of the stereo image B. Next, the processor 7 controls the moving unit 3 on the basis of the three-dimensional position of the tip 20*a* and the control parameter 12 only when the tip 20*a* is positioned outside a predetermined specific region C within the field of view F to change the position and orientation of the endoscope 2, thereby moving the tip 20*a* toward the specific region C. Through such follow-up control, the position of the field of view F is controlled such that the tip 20*a* is continuously arranged within the specific region C.

The control parameter 12 includes a follow-up parameter P. The follow-up parameter P is a parameter related to at least one of a positional relationship between the endoscope 2 and the specific region C or a follow-up speed of the endoscope 2 for a follow-up target. During a surgery, a user operates the user interface 4 to input a desired value of the follow-up parameter P to the control unit 6, thereby enabling the follow-up parameter P to be changed to a desired value.

In the example of FIGS. 3A to 3C, the follow-up parameter P includes a basic distance d, the size of the specific region C, the position of the specific region C on the image B, and the follow-up speed. The basic distance d is a distance between the endoscope 2 and the specific region C and, for example, is a distance in a direction along an optical axis from a tip 2*b* of the endoscope 2 to the center of the three-dimensional specific region C. The size of the specific region C includes sizes Sx, Sy in the lateral direction and the vertical direction on the image B and an actual size Sz in a depth direction. The position of the specific region C on the image B is defined by, for example, two offset amounts Δx, Δy in the lateral direction and the vertical direction from the center of the image B to the center of the specific region C. The follow-up speed is a moving speed of the endoscope 2.

Next, a control method to be executed by the processor 7 will be described.

Figure 4A:
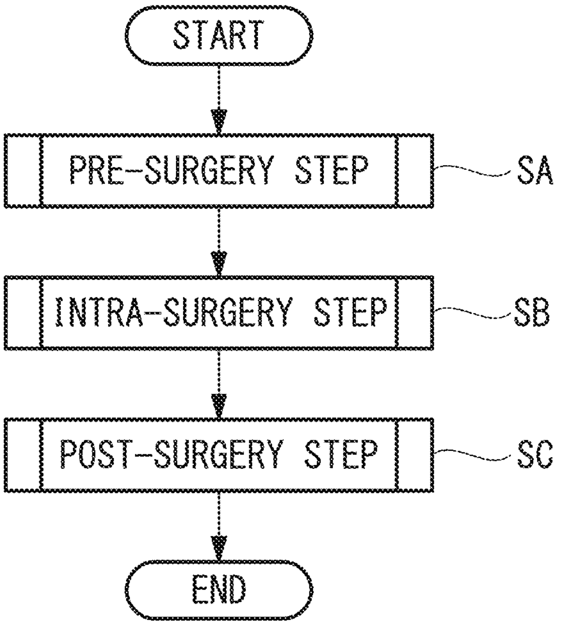
FIG. 4A is a flowchart of a control method according to the first embodiment.

As illustrated in FIG. 4A, the control method according to the present embodiment includes pre-surgery step SA to be executed before a surgery, intra-surgery step SB to be executed during the surgery, and post-surgery step SC to be executed after the surgery.

Figure 4B:
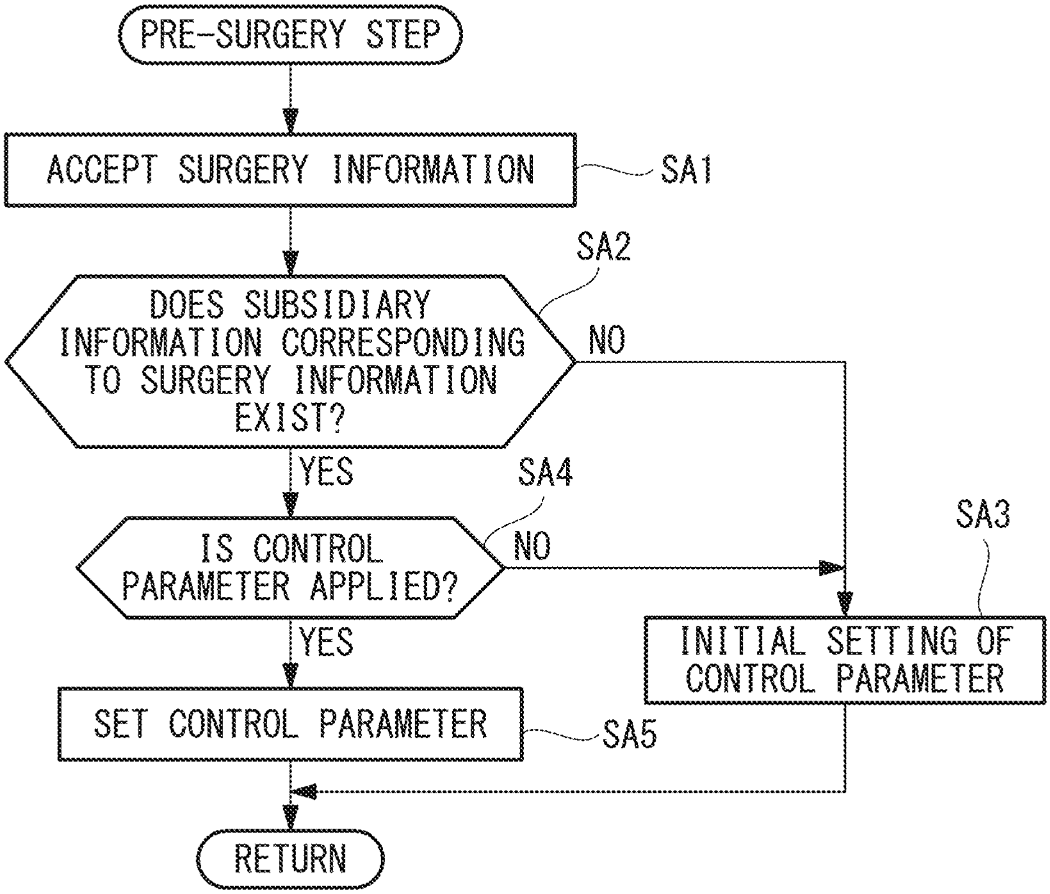
FIG. 4B is a flowchart of pre-surgery step SA in FIG. 4A.

As illustrated in FIG. 4B, pre-surgery step SA includes step SA1 of accepting surgery information and steps SA2 to SA5 of setting the control parameter 12 for a surgery to be performed now.

After the control unit 6 is activated, a user such as a surgeon operates the user interface 4 to input surgery information to the control unit 6. The processor 7 receives the input surgery information (step SA1).

The surgery information is information related to a surgery to be performed now and includes at least one of surgeon information, surgery information, facility information, or patient information. The surgeon information is information related to a surgeon who performs a surgery and includes the name, career, specialized field, and the like of the surgeon. The surgery information includes information related to a surgery region and information related to an operative method. The information related to a surgery region includes, for example, the name of the surgery region, such as large bowel or gallbladder, and the information related to an operative method includes, for example, the name of the operative method, such as sigmoid colectomy or lower anterior resection. The facility information is information related to a facility where the surgery is to be performed and includes the name, the scale (for example, the number of beds), a group relationship, and the like of the facility. The patient information is information related to a patient and includes the name, sex, age, height, and BMI of the patient as well as information related to a level of difficulty of the surgery or the like.

As described, the surgery information includes a plurality of items about the surgeon, operative method, patient, and the like.

Next, the processor 7 sets the control parameter 12 on the basis of the surgery information (steps SA2 to SA5).

Specifically, the processor 7 searches the storage unit 9 for the subsidiary information 13 corresponding to the surgery information at least in terms of a predetermined item. In the present embodiment, the predetermined item at least includes the name of the surgeon. As will be described later, after a surgery through use of the control unit 6 is performed, the control parameter 12 having been adjusted by the surgeon is stored in the storage unit 9 in association with the subsidiary information 13. The subsidiary information 13 is information related to the surgery similarly to the surgery information. When the surgeon initially uses the control unit 6, the subsidiary information 13 corresponding to the surgery information does not exist in the storage unit 9.

In the case where the subsidiary information 13 corresponding to the surgery information does not exist in the storage unit 9 (NO in step SA2), the processor 7 sets the control parameter 12 at an initial value (step SA3). The processor 7 may determine the initial value on the basis of an operation of the user interface 4 performed by the user. For example, the processor 7 may cause the user to select one of a plurality of initial values.

In a case where the subsidiary information 13 corresponding to the surgery information exists in the storage unit 9 (YES in step SA2), the processor 7 proceeds to step SA4. Steps SA4 and SA5 will be described later.

After step SA2, the processor 7 executes intra-surgery step SB.

Figure 4C:
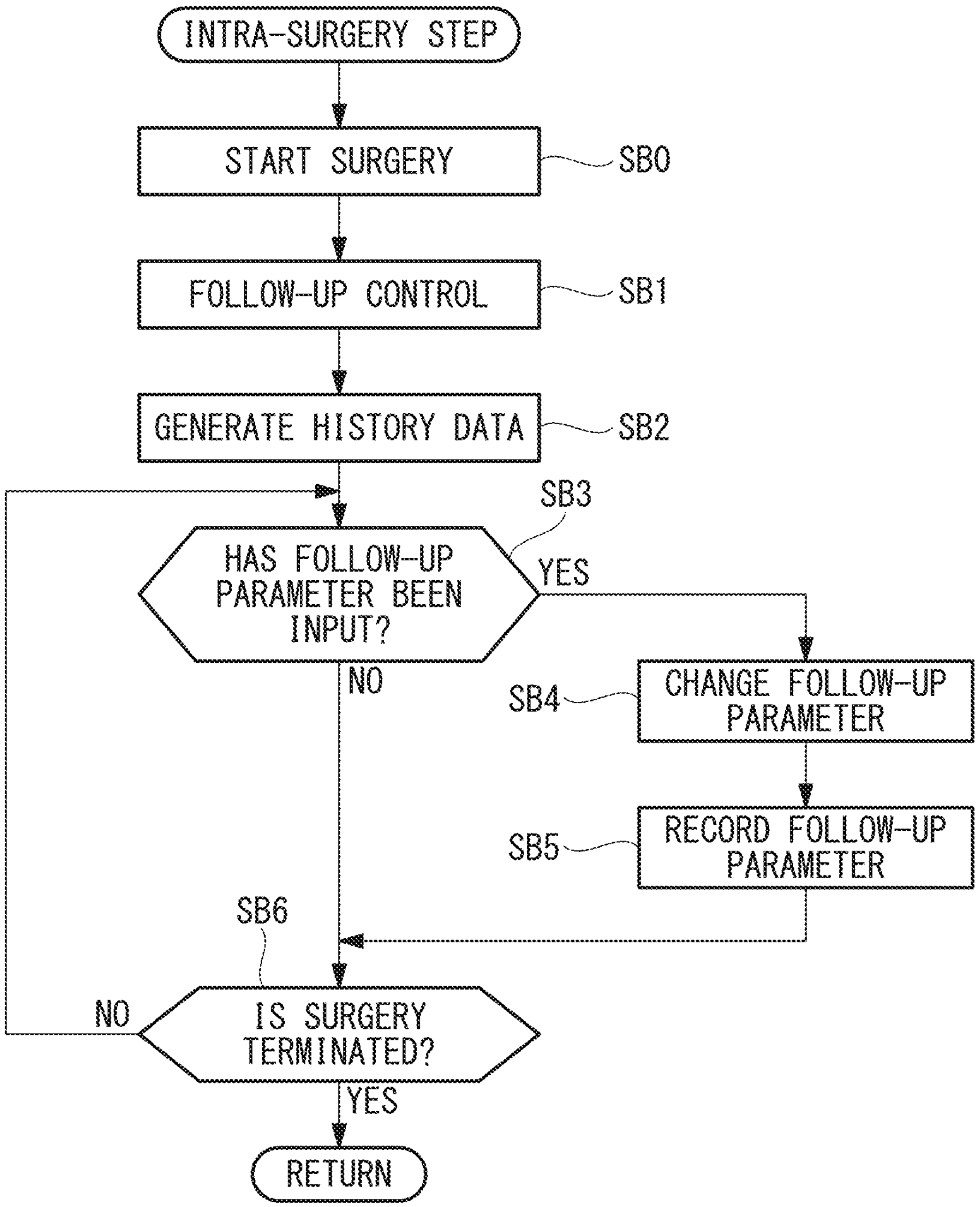
FIG. 4C is a flowchart of intra-surgery step SB in FIG. 4A.

As illustrated in FIG. 4C, intra-surgery step SB includes step SB1 of causing the endoscope 2 to follow a follow-up target on the basis of the control parameter 12, step SB2 of generating the history data 14 on the control parameter 12 during a surgery in the storage unit 9, steps SB3, SB4 of changing the control parameter 12 on the basis of an operation of the user interface 4, and step SB5 of recording the control parameter 12 having been changed.

The processor 7 starts intra-surgery step SB in response to a starting trigger input by an operation of the user interface 4, for example, (step SB0) and then starts the follow-up control (step SB1). The processor 7 performs the follow-up control on the basis of the control parameter 12 set in pre-surgery step SA, for example, on the basis of the control parameter 12 initially set.

After starting the follow-up control, the processor 7 generates the history data 14 (step SB2) and accepts a change in the follow-up parameter P based on an operation of the user interface 4 (step SB3).

Specifically, the processor 7 generates, in the storage unit 9, the history data 14 for recording a value of the follow-up parameter P during the surgery (step SB2).

When intending to change the follow-up parameter P, the user operates the user interface 4 to input a desired value of the follow-up parameter P to the control unit 6. The processor 7 receives the input value (YES in step SB3) and changes the value of the follow-up parameter P to the input value (step SB4). The follow-up parameter P is thereby adjusted to the user desired value, and the processor 7 performs the follow-up control on the basis of the follow-up parameter P after being adjusted. The processor 7 also records the input value of the follow-up parameter P in the history data 14 (step SB5).

Figure 5:
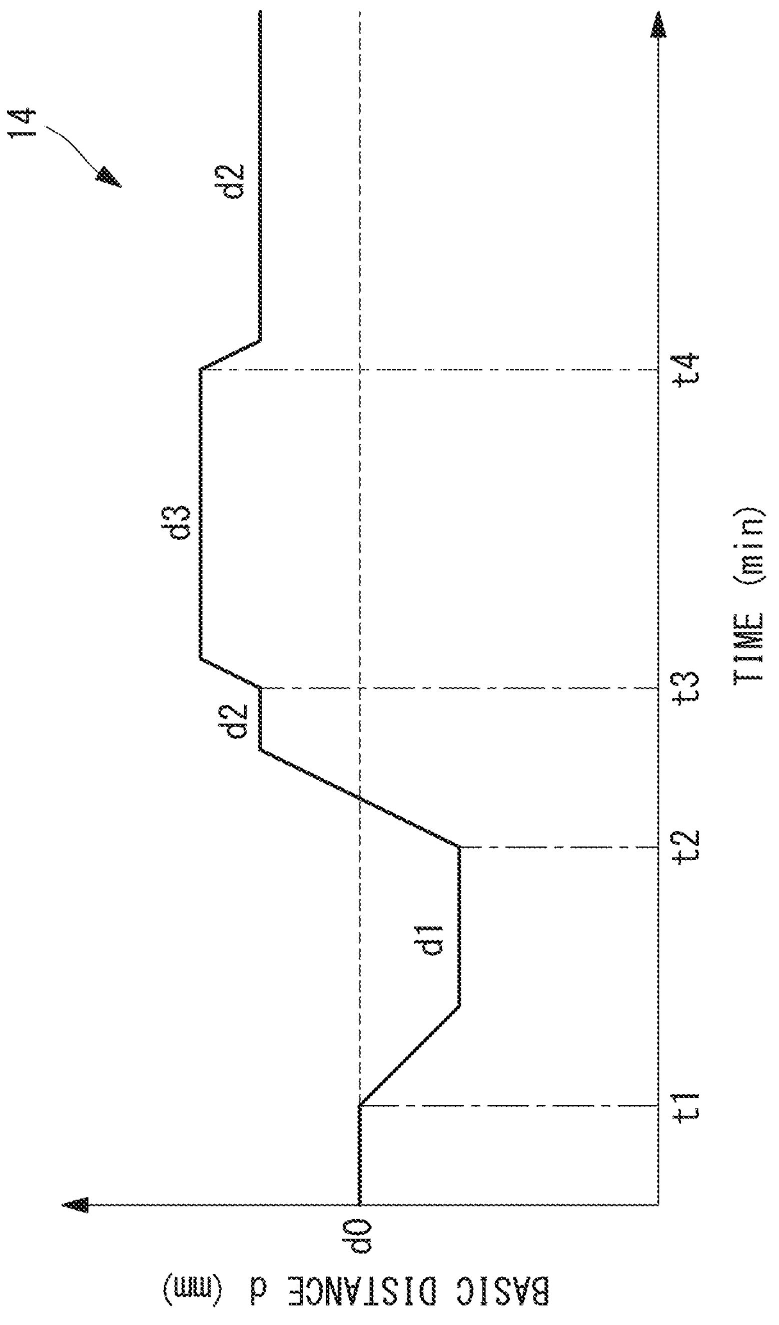
FIG. 5 is a diagram illustrating an example of history data in the first embodiment.

The history data 14 generated as described above is an operation log of the user interface 4 indicating a history of operations of the user interface 4 performed by the surgeon for changing the follow-up parameter P. FIG. 5 is an example of an operation log 14 indicating a history of changes in the basic distance d, the horizontal axis indicating the time period from the start of a surgery and the vertical axis indicating the basic distance d. In this example, the basic distance d is changed from an initial value do to distances d1, d2, and d3. The basic distance d (d0, d1, d2, d3) may be recorded in association with the time period from the start of a surgery.

The processor 7 terminates intra-surgery step SB in response to a termination trigger input to the user interface 4 by the user, for example, (YES in step SB6) and then starts post-surgery step SC.

Figure 4D:
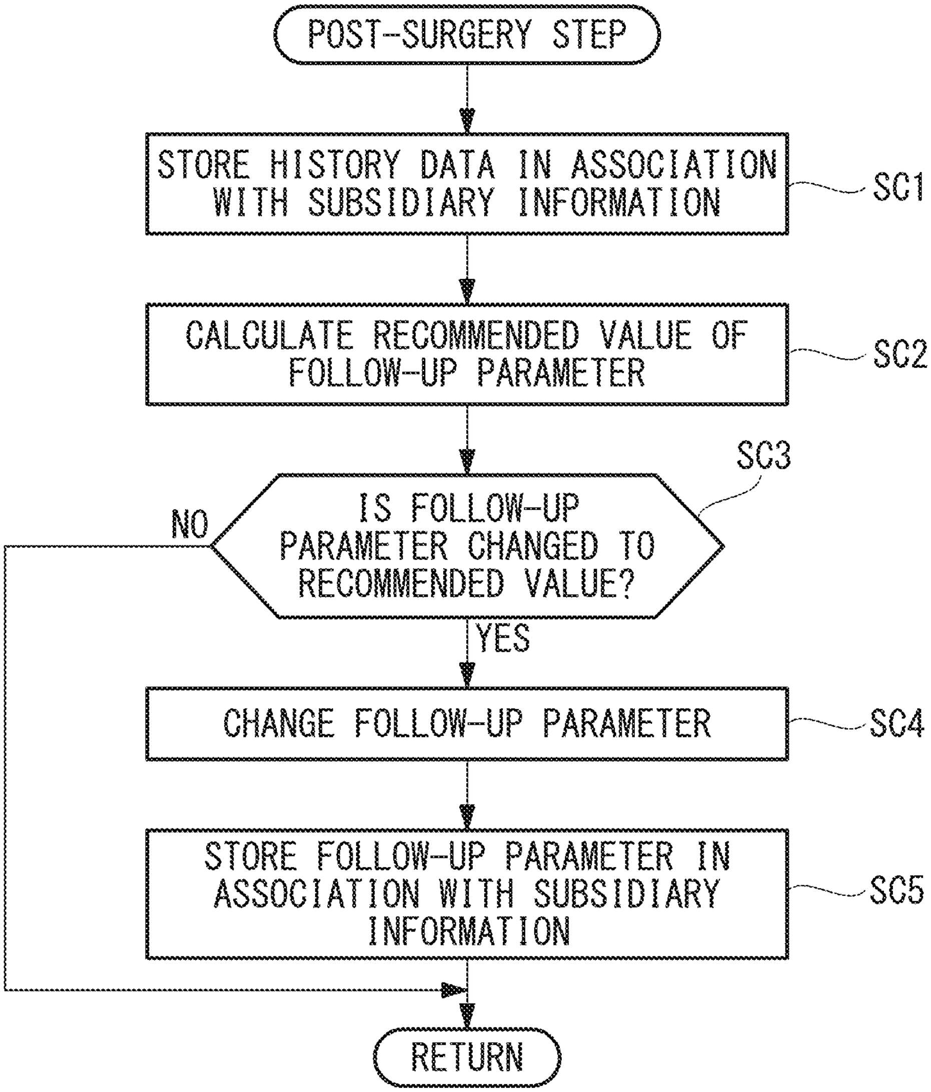
FIG. 4D is flowchart of post-surgery step SC in FIG. 4A.

As illustrated in FIG. 4D, post-surgery step SC includes step SC1 of causing the storage unit 9 to store the history data 14 in association with the subsidiary information, step SC2 of calculating a recommended value of the follow-up parameter P from the history data 14, step SC3 of inquiring of the user whether or not to change the follow-up parameter P to the recommended value, step SC4 of changing the follow-up parameter P on the basis of a response from the user, and step SC5 of recording the follow-up parameter P having been changed in the storage unit 9 in association with the subsidiary information 13.

The processor 7 causes the storage unit 9 to store the history data 14 generated in intra-surgery step SB in association with the subsidiary information 13 (step SC1). The subsidiary information 13 is at least part of the surgery information input in step SA1 and at least includes the surgeon information. The subsidiary information 13 may be set by the user.

Next, the processor 7 calculates an average of the follow-up parameters P changed by the user as the recommended value (step SC2). In the case of the basic distance d in FIG. 5, the recommended value is the average of the distances d1, d2, and d3. The recommended value may be a value other than the average and may be, for example, a median, a mode, a value used for the longest usage time, or a time-weighted average ρyi·ti/Σti weighted by a usage time of the follow-up parameters P in the operation log 14, where yi is the value of the follow-up parameter P, and ti is the length of the usage time of the follow-up parameter yi.

Next, the processor 7 displays an inquiry to the user by, for example, displaying an optical display as to "whether or not to change the follow-up parameter" on the display unit 5 or outputting a sound as to "whether or not to change the follow-up parameter" (step SC3). The processor 7 may make the inquiry to the user using any other means. The user operates the user interface 4 to input a response to the inquiry to the control unit 6.

In a case where a response that the change is made is accepted (YES in step SC3), the processor 7 changes the follow-up parameter P to the recommended value (step SC4) and causes the storage unit 9 to store the changed follow-up parameter P in association with the subsidiary information 13 (step SC5). The follow-up parameter P adjusted by the surgeon is thereby stored in the storage unit 9 in association with information about the surgeon.

On the other hand, in a case where a response that the change is not made is accepted (NO in step SC3), the processor 7 terminates post-surgery step SC without performing steps SC4, SC5.

When steps SC1 to SC5 above are executed, the history data 14 associated with the subsidiary information 13 and the follow-up parameter P having been adjusted are stored in the storage unit 9 after a surgery through use of the control unit 6.

When the control unit 6 is used after the follow-up parameter P having been adjusted is stored in the storage unit 9, the processor 7 sets the follow-up parameter P on the basis of the surgery information in pre-surgery step SA (steps SA2, SA4, SA5).

Specifically, in the case where the subsidiary information 13 corresponding to the surgery information at least in terms of the name of the surgeon exists (YES in step SA2), the processor 7 inquires of the user whether or not to apply the follow-up parameter P associated with the subsidiary information 13 corresponding to the surgery information to a surgery to be performed now (step SA4), thereby proposing, to the surgeon, the use of the follow-up parameter P adjusted previously by the surgeon himself/herself.

The user operates the user interface 4 to input a response to the inquiry to the control unit 6.

In a case where a response that the application is performed is accepted (YES in step SA4), the processor 7 sets the associated follow-up parameter P as the follow-up parameter P of a surgery to be performed now (step SA5). The surgeon can thereby use the follow-up parameter P adjusted in a previous surgery by himself/herself in a surgery to be performed now.

On the other hand, in a case where a response that the application is not performed is accepted (NO in step SA4), the processor 7 sets the follow-up parameter P at the initial value (step SA3).

It is important in an endoscopic surgery to maintain an appropriate field of view of an endoscope, and an appropriate control parameter therefor varies depending on conditions such as a surgeon, an operative method, a target organ, a facility where the surgery is to be performed, and a patient. Consequently, adjustment of the control parameter requires the labor of the surgeon. For example, in a case where a scopist manually operates the endoscope, the labor of causing the scopist to experience a plurality of surgeries in advance for education and the labor of a surgeon instructing the scopist about an operation of the endoscope during a surgery are required. In a case of automatically controlling the field of view of the endoscope, adjustment or the like of the control parameter is required by setting a surgeon's preferred control parameter in advance, operating the user interface by the surgeon during the surgery, or the like.

According to the present embodiment, the history data 14 indicating the history of changes in the follow-up parameter P by the surgeon is stored in the storage unit 9 in association with the subsidiary information 13 during the surgery, and the recommended value of the follow-up parameter P is calculated from the history data 14. The appropriate follow-up parameter P can thereby be obtained without requiring the labor of the surgeon.

In addition, according to the present embodiment, the follow-up parameter P changed to the recommended value is stored in the storage unit 9 in association with the subsidiary information 13 after the surgery, and the use of the changed follow-up parameter P is proposed to the surgeon in a surgery to be performed subsequently. Consequently, in the next and subsequent surgeries, the surgeon can use the follow-up parameter P adjusted by himself/herself from the start of the surgeries, which can save the labor of adjusting the follow-up parameter P.

In addition, according to the present embodiment, the processor 7 inquires of the user whether or not to change the follow-up parameter P to the recommended value, and the user determines whether or not to make a change. The follow-up parameter P can thereby be changed only when the user desires. The recommended value is not necessarily a preferable value, and it is desirable not to make a change to the recommended value in some cases.

Similarly, the processor 7 inquires of the user whether or not to apply the changed follow-up parameter P to a surgery to be performed now, and the user determines whether or not to perform the application. The follow-up parameter P having been adjusted can thereby be applied to a surgery to be performed now only when the user desires.

Second Embodiment

Next, an endoscope system, a control method, and a control program according to a second embodiment of the present disclosure will be described.

The present embodiment is different from the first embodiment in terms of a control parameter for which a recommended value is calculated. In the present embodiment, components different from the components of the first embodiment will be described, and components common to the components of the first embodiment are denoted by the same reference characters and description thereof will be omitted.

The endoscope system 1 according to the present embodiment includes the endoscope 2, the moving unit 3, the user interface 4, the display unit 5, and the control unit 6, similarly to the first embodiment.

The control parameter 12 includes a unit change amount Δ of the follow-up parameter P in addition to the follow-up parameter P. The unit change amount Δ is a change amount of the follow-up parameter P for each operation of the user interface 4. The processor 7 changes the follow-up parameter P by the unit change amount Δ for each operation of the user interface 4. Consequently, in the case of the basic distance d, for example, the user can change the basic distance d by the distance Δ each time he/she operates the user interface 4.

Next, the control method to be executed by the processor 7 will be described.

The control method according to the present embodiment includes pre-surgery step SA, intra-surgery step SB, and post-surgery step SC similarly to the first embodiment.

Figure 6A:
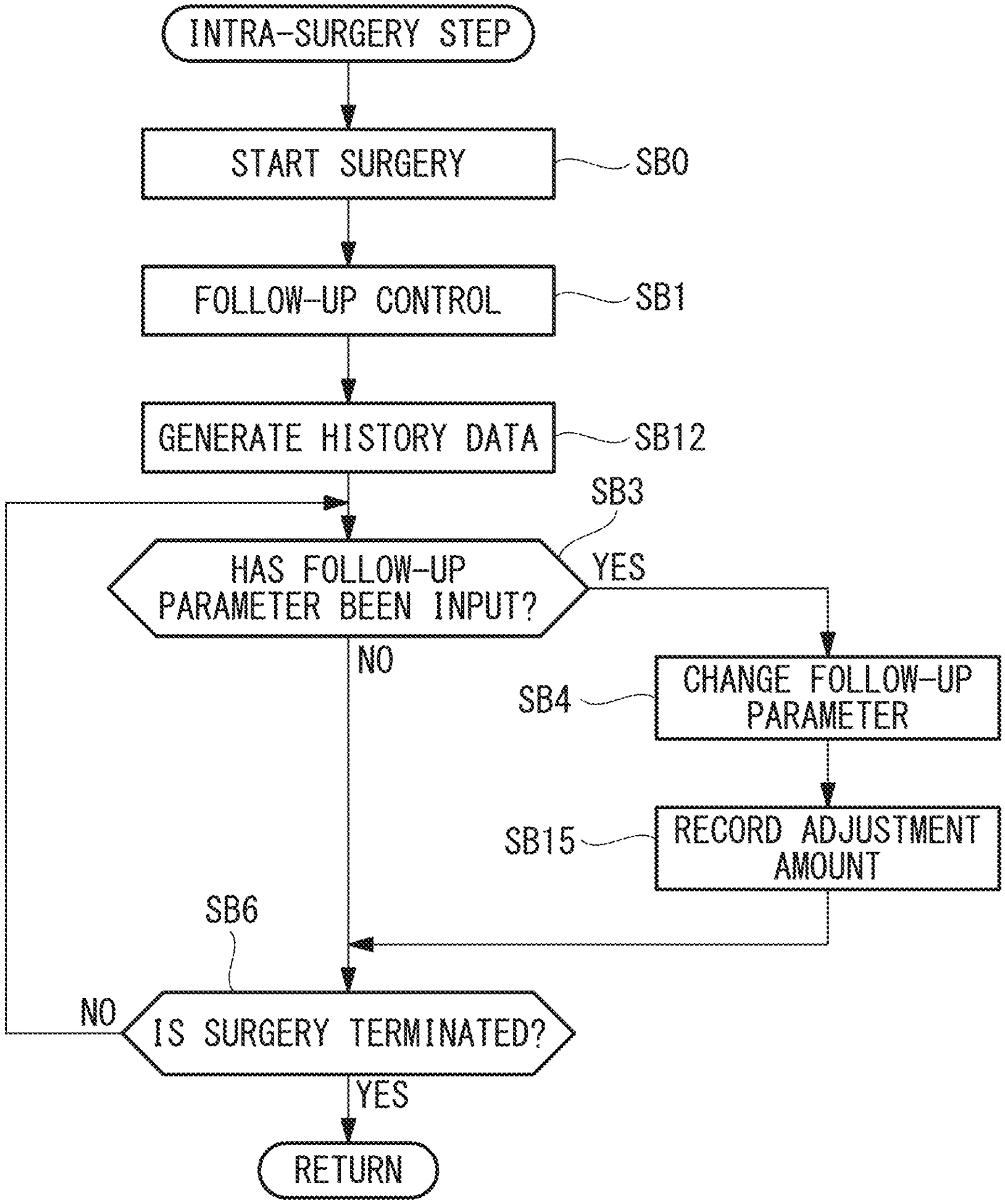
FIG. 6A is a flowchart of intra-surgery step SB in a control method according to a second embodiment.
Figure 6B:
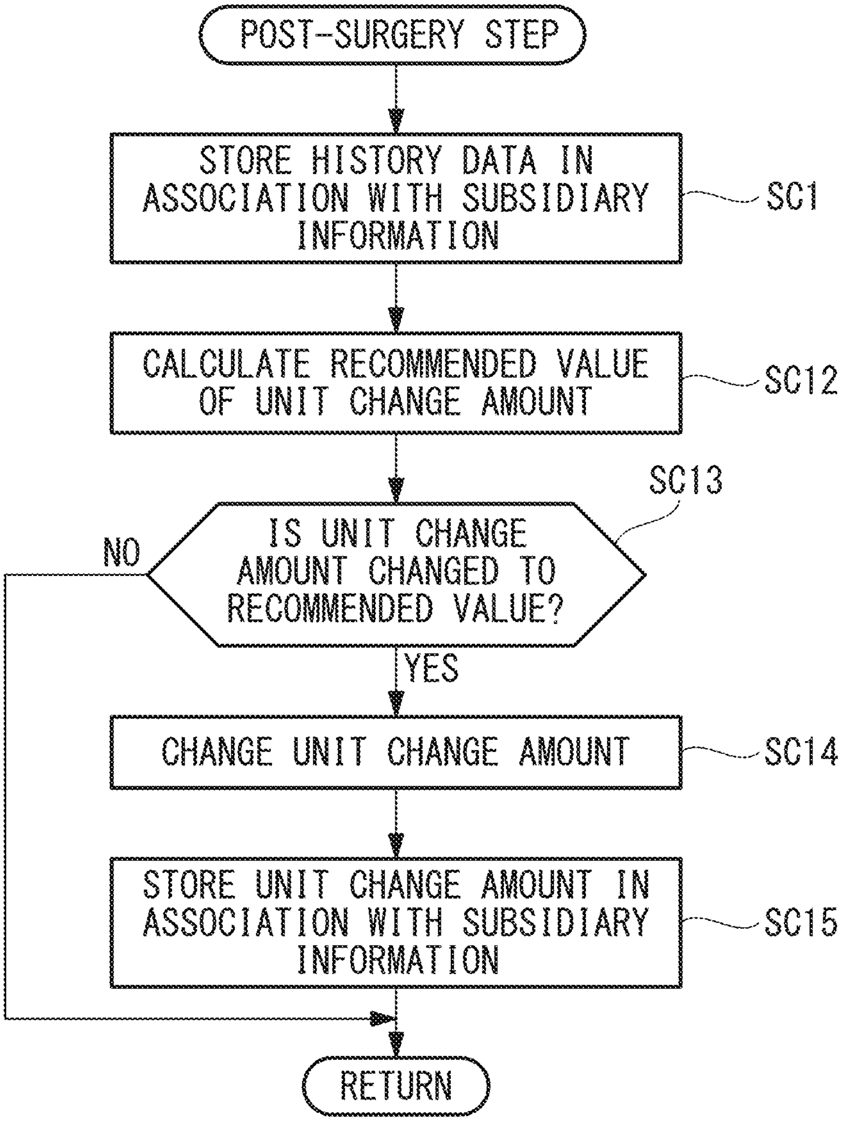
FIG. 6B is a flowchart of post-surgery step SC in the control method according to the second embodiment.

FIGS. 6A and 6B illustrate intra-surgery step SB and post-surgery step SC in the present embodiment, respectively.

As illustrated in FIG. 6A, intra-surgery step SB includes step SB1, step SB12 of generating, in the storage unit 9, the history data 14 on the follow-up parameter P during a surgery, steps SB3, SB4 of changing the follow-up parameter P on the basis of an operation of the user interface 4, and step SB15 of recording an adjustment amount of the follow-up parameter P.

The processor 7 generates the history data 14 (step SB12), accepts a change in the follow-up parameter P (step SB3), and changes the follow-up parameter P on the basis of an operation of the user interface 4 (step SB4).

Specifically, the processor 7 generates, in the storage unit 9, the history data 14 for recording an adjustment amount of the follow-up parameter P (step SB12).

In a case where the unit change amount Δ initially set is excessively small, the user operates the user interface 4 consecutively a plurality of times in a single adjustment of the follow-up parameter P. Consecutive operations indicate that, for example, a time interval between an i-th operation and the next i+1-th operation is less than or equal to a predetermined threshold value. The adjustment amount is a change amount of the follow-up parameter P in a single adjustment and is, for example, a change amount of the follow-up parameter P within a predetermined time period. The processor 7 may calculate, as the adjustment amount, a product of the unit change amount Δ and the number of consecutive operations of the user interface 4. After step SB4, the processor 7 calculates the adjustment amount of the follow-up parameter P and records the adjustment amount in the history data 14 (step SB15).

Figure 7:
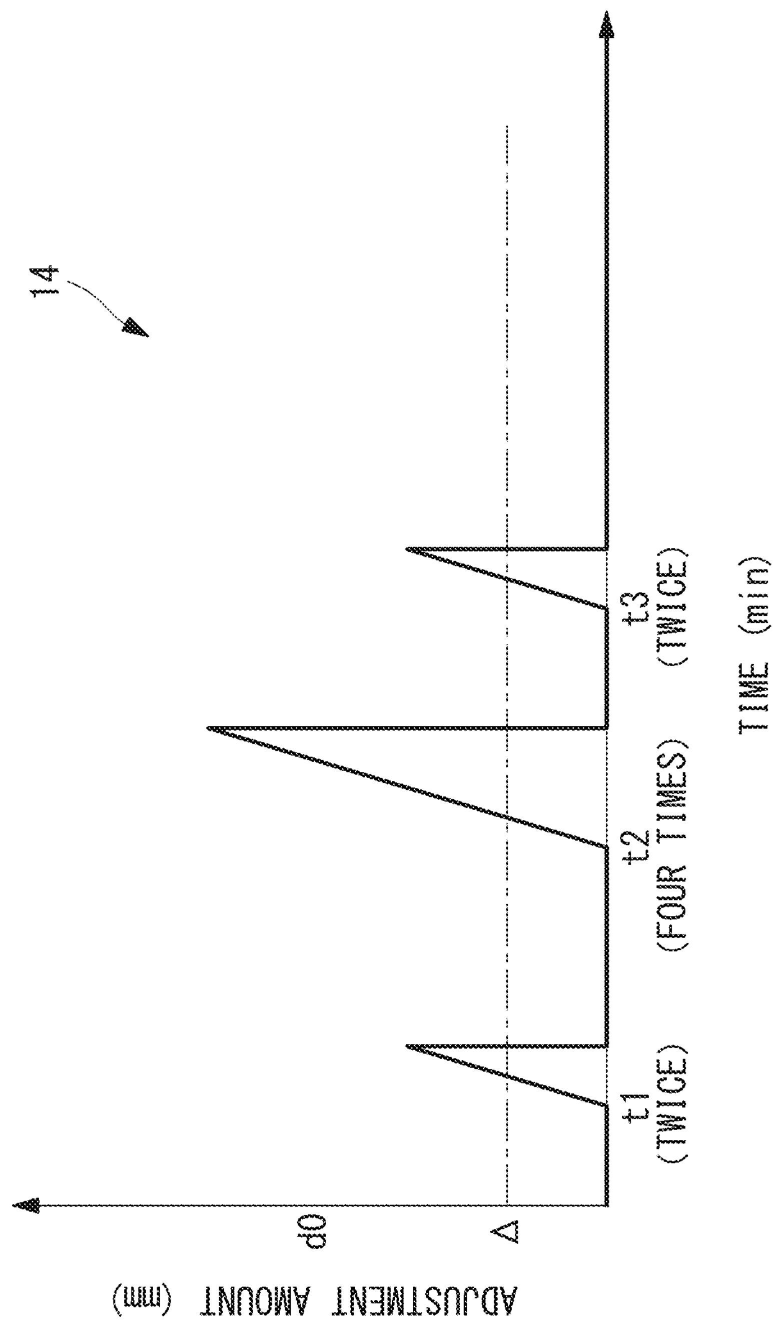
FIG. 7 is a diagram illustrating an example of history data in the second embodiment.

FIG. 7 illustrates an example of the history data 14. In FIG. 7, in the first (t1) and third (t3) adjustments, the basic distance d is changed by twice the unit change amount Δ through two consecutive operations. In the second adjustment (t2), the basic distance d is changed by four times the unit change amount Δ through four consecutive operations.

As illustrated in FIG. 6B, post-surgery step SC includes step SC1, step SC12 of calculating a recommended value of the unit change amount Δ from the history data 14, step SC13 of inquiring of a user whether or not to change the unit change amount Δ to the recommended value, step SC14 of changing the unit change amount Δ on the basis of a response from the user, and step SC15 of storing the unit change amount Δ in the storage unit 9 in association with the subsidiary information 13.

The processor 7 calculates a mode of adjustment amounts in the history data 14 as the recommended value (step SC12). Since two consecutive operations are performed most often in the example of FIG. 7, for example, the mode is a value twice the unit change amount Δ. The recommended value may be a value other than the mode and may be, for example, an average of a maximum value and a minimum value, a median, the greatest common divisor value, an approximation having a minimum error from each adjustment amount, or a time-weighted average $\Sigma yi \cdot ti/\Sigma ti$ weighted by a usage time of the adjustment amount, where yi is the adjustment amount, and ti is the length of the usage time of the adjustment amount yi.

Next, the processor 7 displays an inquiry to the user by displaying an optical display on the display unit 5 or outputting a sound, for example, similarly to step SC3 (step SC13). The user inputs a response to the inquiry to the control unit 6 using the user interface 4.

In a case where a response that the change is made is accepted (YES in step SC13), the processor 7 changes the unit change amount Δ to the recommended value (step SC14) and causes the storage unit 9 to store the changed unit change amount Δ in association with the subsidiary information 13 (step SC15).

On the other hand, in a case where a response that the change is not made is accepted (NO in step SC13), the processor 7 terminates post-surgery step SC without performing steps SC14 and SC15.

When steps SC1 and SC12 to SC15 above are executed, the unit change amount Δ having been adjusted and associated with the subsidiary information 13 is newly stored in the storage unit 9 after a surgery through use of the control unit 6.

When the control unit 6 is used after the unit change amount Δ having been adjusted is stored in the storage unit 9, the processor 7 sets the unit change amount Δ on the basis of the surgery information in pre-surgery step SA (steps SA2, SA4, SA5).

Specifically, in the case where the subsidiary information 13 corresponding to the surgery information at least in terms of the name of the surgeon exists (YES in step SA2), the processor 7 inquires of the user whether or not to apply the unit change amount Δ associated with the subsidiary information 13 corresponding to the surgery information to a surgery to be performed now (step SA4), thereby proposing, to the surgeon, the use of the unit change amount Δ adjusted previously by the surgeon himself/herself.

In a case where a response that the application is performed is accepted (YES in step SA4), the processor 7 sets the associated unit change amount Δ as the unit change amount Δ in a surgery to be performed now (step SA5). The surgeon can thereby use, in the surgery to be performed now, the unit change amount Δ adjusted in a previous surgery by himself/herself.

On the other hand, in a case where a response that the application is not performed is accepted (NO in step SA4), the processor 7 sets the unit change amount Δ at the initial value (step SA3).

As described, according to the present embodiment, the history data 14 indicating a history of the adjustment amount of the follow-up parameter P adjusted by the surgeon is stored in the storage unit 9 in association with the subsidiary information 13 during the surgery, and the recommended value of the unit change amount Δ is calculated from the history data 14. The appropriate unit change amount Δ can thereby be obtained without requiring the labor of the surgeon.

In addition, according to the present embodiment, the unit change amount Δ changed to the recommended value is stored in the storage unit 9 in association with the subsidiary information 13 after the surgery, and in a surgery to be performed subsequently, the use of the changed unit change amount Δ is proposed to the surgeon. Consequently, the surgeon can use the unit change amount Δ adjusted by himself/herself from the start of surgeries in the next and subsequent surgeries, which can save the labor of adjusting the unit change amount Δ.

In addition, according to the present embodiment, the processor 7 inquires of the user whether or not to change the unit change amount Δ to the recommended value, and the user determines whether or not to make a change. The unit change amount Δ can thereby be changed only when the user desires.

Similarly, the processor 7 inquires of the user whether or not to apply the changed unit change amount Δ to a surgery to be performed now, and the user determines whether or not to perform the application. The unit change amount Δ having been adjusted can thereby be applied to a surgery to be performed now only when the user desires.

Third Embodiment

Next, an endoscope system, a control method, and a control program according to a third embodiment of the present disclosure will be described.

The present embodiment is different from the first and second embodiments in terms of history data to be used for calculating the recommended value. In the present embodiment, components different from the components of the first embodiment will be described, and components common to the components of the first embodiment are denoted by the same reference characters and description thereof will be omitted.

The endoscope system according to the present embodiment includes the endoscope 2, the moving unit 3, the user interface 4, the display unit 5, and the control unit 6 similarly to the first embodiment.

In the present embodiment, the history data 14 is an image group composed of time-series images B during a surgery or a history of the control parameter 12 detected from the respective images B in the image group or information correlated therewith.

Next, the control method to be executed by the processor 7 will be described.

The control method according to the present embodiment includes pre-surgery step SA, intra-surgery step SB, and post-surgery step SC similarly to the first embodiment.

Figure 8A:
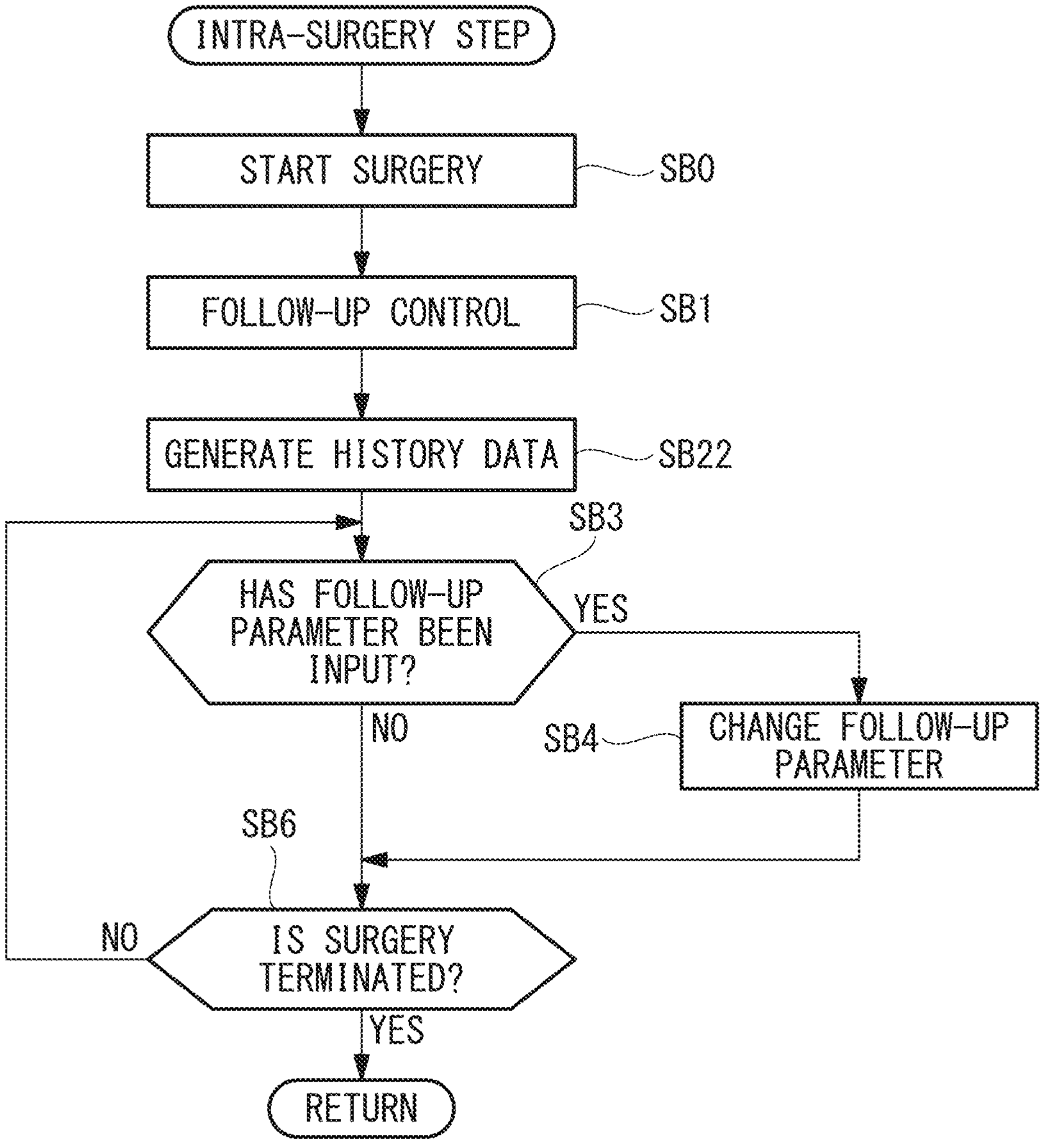
FIG. 8A is a flowchart of intra-surgery step SB in a control method according to a third embodiment.
Figure 8B:
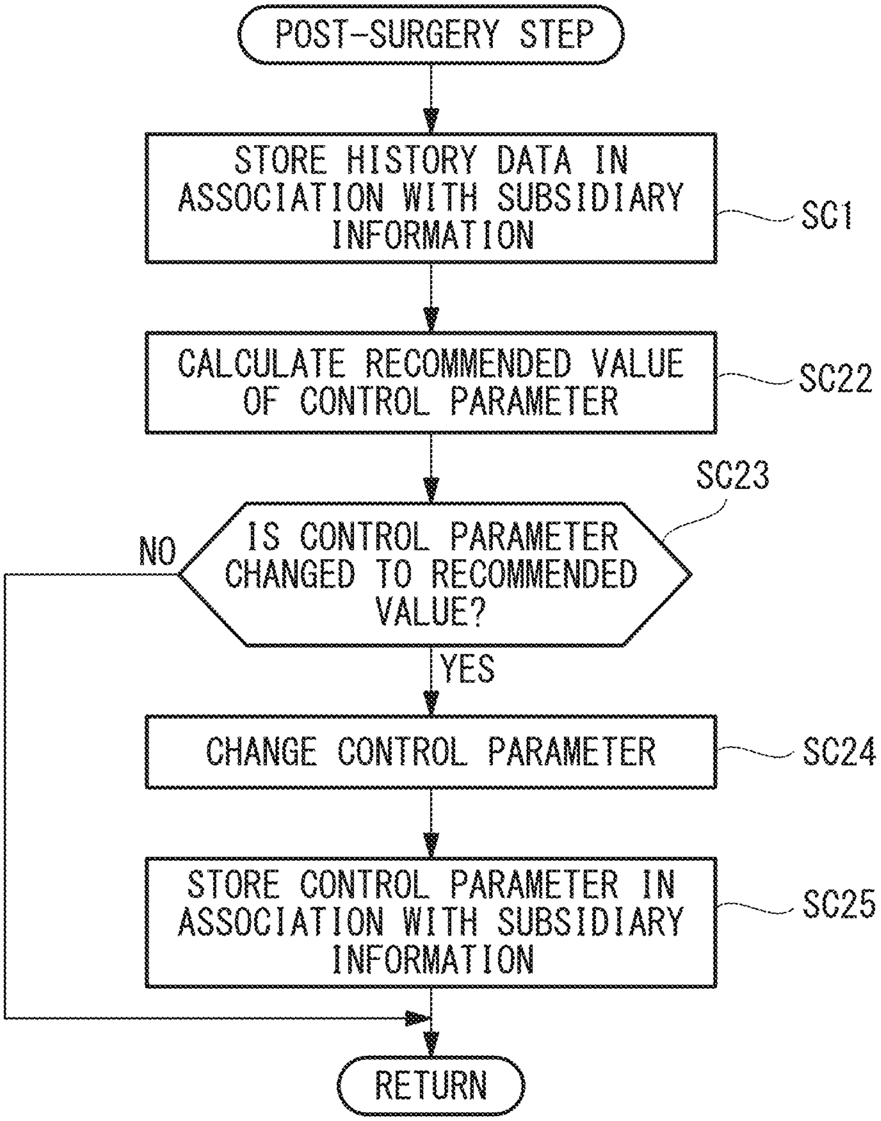
FIG. 8B is a flowchart of post-surgery step SC in the control method according to the third embodiment.

FIGS. 8A and 8B illustrate intra-surgery step SB and post-surgery step SC in the present embodiment, respectively.

As illustrated in FIG. 8A, intra-surgery step SB includes step SB1, step SB22 of generating the history data 14 in the storage unit 9, and steps SB3, SB4.

The processor 7 causes the storage unit 9 to store the image B input from the endoscope 2 to the control unit 6, thereby generating, in the storage unit 9, the image group composed of the time-series images B in intra-surgery step SB as the history data 14 (step SB22).

As illustrated in FIG. 8B, post-surgery step SC includes step SC1, step SC22 of calculating the recommended value of the control parameter 12 from the history data 14, step SC23 of inquiring of a user whether or not to change the control parameter 12 to the recommended value, step SC24 of changing the control parameter 12 on the basis of a response from the user, and step SC25 of storing the changed control parameter 12 in the storage unit 9 in association with the subsidiary information 13.

The processor 7 detects the control parameter 12 or the information correlated with the control parameter 12 and a scene feature from each of the images B as the history data 14 stored in the storage unit 9, and calculates the recommended value of the control parameter 12 for each scene (step SC22). The control parameter 12 is at least one of the follow-up parameter P or the unit change amount Δ, for example.

For example, the processor 7 detects a distance d' (see FIG. 3B) from the endoscope 2 to a predetermined goal as the information correlated with the control parameter 12. The predetermined goal is a follow-up target in the image B, for example, and the distance d' also changes along with a change in the basic distance d. The processor 7 analyzes each of the images B using a publicly-known means to calculate the distance d'. For example, the processor 7 may calculate the distance d' by stereo measurement through use of the stereo images B. Alternatively, the processor 7 may calculate the distance d' from each of the images B using a learning model. The learning model is generated by machine learning (for example, deep learning) of various images B and distances d' and is stored in the storage unit 9 beforehand.

Figure 9A:
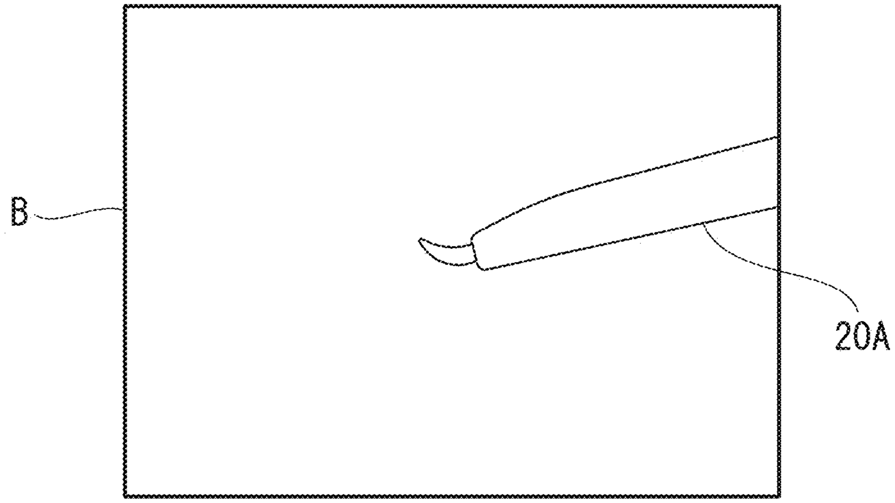
FIG. 9A is a diagram describing an example of a method for detecting a scene feature.
Figure 9B:
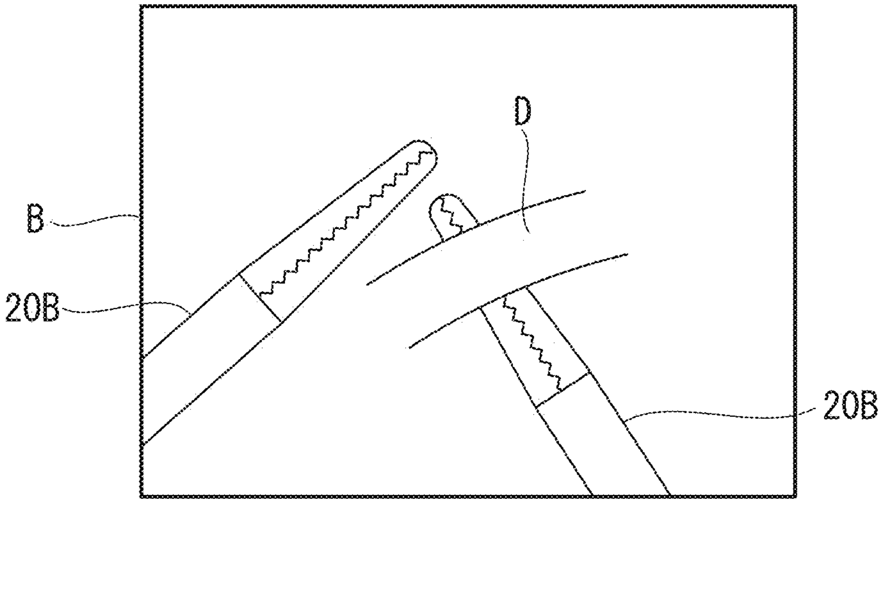
FIG. 9B is a diagram describing another example of the method for detecting a scene feature.
Figure 9C:
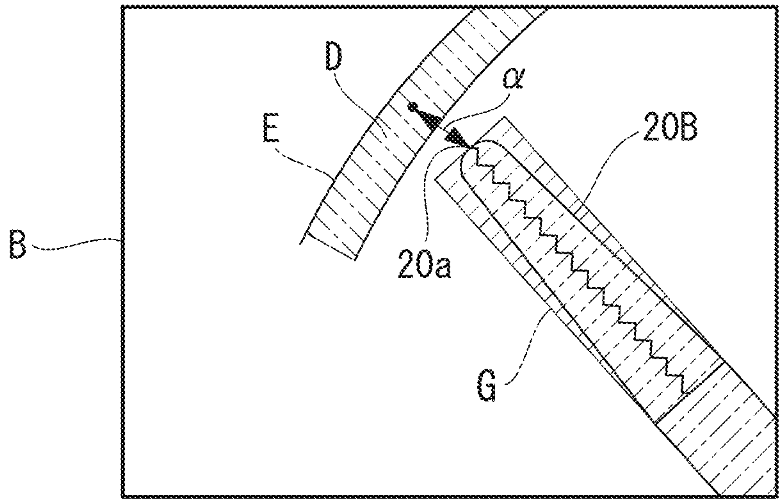
FIG. 9C is a diagram describing another example of the method for detecting a scene feature.

As illustrated in FIGS. 9A to 9C, a surgery commonly includes a plurality of scenes.

FIG. 9A illustrates a scene of cutting a membrane using an electrocautery 20A, and FIG. 9B illustrates a scene of ablating a blood vessel D using forceps 20B. An example of a scene feature is a body tissue (such as a blood vessel or an organ) in the image B and the surgical instruments 20A, 20B. The processor 7 detects the type of at least one of the body tissue or the surgical instruments 20A, 20B in each of the images B using a publicly-known image recognition technology, for example.

FIG. 9C illustrates a scene of treating the blood vessel using the forceps 20B. Another example of a scene feature is that a distance α between a predetermined body tissue and the tip 20*a* of the surgical instrument 20B is less than or equal to a predetermined threshold value. For example, the processor 7 recognizes a region E of the blood vessel D and a region G of the surgical instrument 20B in the image B, calculates the distance α between the center of gravity of the region E and the tip 20*a*, and in a case where the distance α is less than or equal to the threshold value, detects that fact as a feature.

Next, the processor 7 calculates, for each detected scene feature, an average of the control parameter 12 or the information correlated therewith, for example, an average of the distances d', as the recommended value. The recommended value of the control parameter 12 suitable for each scene is thereby calculated.

The recommended value may be a value other than the average and may be, for example, a median, a mode, a value used for the longest usage time, or a time-weighted average $\Sigma yi \cdot ti/\Sigma ti$ weighted by a usage time of the control parameter 12 or the information correlated therewith, where yi is the value of the control parameter 12, and ti is the length of the usage time of the control parameter yi.

Next, the processor 7 displays an inquiry to the user by displaying an optical display on the display unit 5 or outputting a sound, for example, similarly to step SC3 (step SC23). The user inputs a response to the inquiry to the control unit 6 using the user interface 4.

In a case where a response that the change is made is accepted (YES in step SC23), the processor 7 changes the control parameter 12 to the recommended value (step SC24) and causes the storage unit 9 to store the changed control parameter 12 in association with the subsidiary information 13 and a scene feature (step SC25).

On the other hand, in a case where a response that the change is not made is accepted (NO in step SC23), the processor 7 terminates post-surgery step SC without performing steps SC24 and SC25.

When the control unit 6 is used after the control parameter 12 is stored in the storage unit 9 in association with the scene feature, the processor 7 sets the control parameter 12 on the basis of the surgery information and the response from the user in pre-surgery step SA (steps SA2 to SA5).

In a case where the control parameter 12 having been adjusted is set as the control parameter 12 of a surgery to be performed now (step SA5), the processor 7, in intra-surgery step SB, detects a scene feature from the image B and controls the moving unit 3 on the basis of the control parameter 12 in accordance with the feature. The control parameter 12, for example, the follow-up parameter P such as the basic distance d, is thereby changed automatically to an appropriate value in accordance with the scene during the surgery.

As described, according to the present embodiment, the image B during the surgery is stored in the storage unit 9 as the history data 14 in association with the subsidiary information 13, and the recommended value of the control parameter 12 in each scene is calculated from the history data 14. The appropriate control parameter 12 can thereby be obtained without requiring the labor of the surgeon.

In addition, according to the present embodiment, the control parameter 12 changed to the recommended value is stored in the storage unit 9 in association with the subsidiary information 13 after the surgery, and in a surgery to be performed subsequently, whether or not to use the changed control parameter 12 is proposed to the surgeon. Consequently, the surgeon can use the control parameter 12 adjusted by himself/herself from the start of surgeries in the next and subsequent surgeries, which can save the labor of adjusting the control parameter 12.

In addition, according to the present embodiment, the processor 7 inquires of the user whether or not to change the control parameter 12 to the recommended value, and the user determines whether or not to make a change. The control parameter 12 can thereby be changed only when the user desires.

Similarly, the processor 7 inquires of the user whether or not to apply the changed control parameter 12 to a surgery to be performed now, and the user determines whether or not to perform the application. The control parameter 12 having been adjusted can thereby be applied to the surgery to be performed now only when the user desires.

It has been described in the present embodiment that the processor 7 stores the image B in intra-surgery step SB as the history data 14. Instead of this, the control parameter 12 or the information correlated with the control parameter 12 and the scene feature may be stored as the history data 14.

In other words, in intra-surgery step SB, the processor 7 detects the control parameter 12 or the information correlated therewith and a scene feature from each of the images B input from the endoscope 2 to the control unit 6 and causes the storage unit 9 to store the control parameter 12 or the information correlated therewith and the scene feature which have been detected as the history data 14. In post-surgery step SC, the processor 7 calculates the recommended value of the control parameter 12 of each scene from the history data 14.

It has been described in each of the above-described embodiments that the processor 7 changes the control parameter 12 to the recommended value on the basis of a response from the user. Instead of this, the control parameter 12 may be changed automatically to the recommended value without inquiring of the user whether or not to change the control parameter 12. In this case, step SC3, SC13, or SC23 is omitted in each of the embodiments.

Similarly, in each of the embodiments, the processor 7 may apply the control parameter 12 associated with the subsidiary information corresponding to the surgery information to a surgery to be performed now without inquiring of the user. In this case, step SA4 is omitted in each of the embodiments.

It has been described in each of the above-described embodiments that the processor 7 calculates the recommended value in post-surgery step SC. Instead of this, the recommended value may be calculated in pre-surgery step SA.

In this case, the processor 7 executes steps SC2 to SC4, SC12 to SC14, or SC22 to SC24 in pre-surgery step SA in a surgery to be performed subsequently. In other words, in pre-surgery step SA, the processor 7 reads out the history data 14 associated with the subsidiary information 13 corresponding to the surgery information from the storage unit 9, calculates the recommended value of the control parameter 12 from the history data 14, and inquires of the user whether or not to change the control parameter 12 to the recommended value.

With such a configuration, the surgeon can use, from the start of a surgery, the appropriate control parameter 12 adjusted by himself/herself in a previous surgery, which can save the labor of adjusting the control parameter 12.

There is a plurality of types of the surgical instruments 20 that may be used in a surgery. Consequently, there is a plurality of types of the surgical instruments 20 that may be follow-up targets. The preferable control parameter 12 may vary for each type of the surgical instruments 20. Consequently, in each of the embodiments, the processor 7 may select the surgical instrument 20 to which the control parameter 12 having been adjusted is to be applied on the basis of the type of the surgical instrument 20.

Figure 10A:
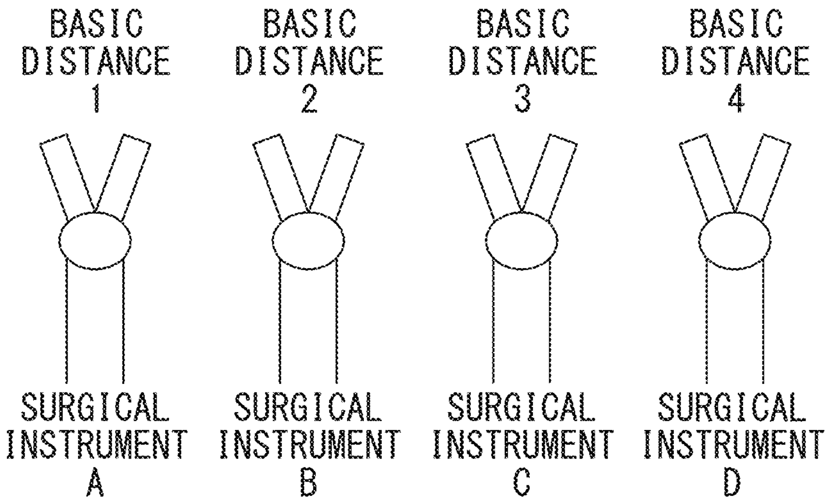
FIG. 10A is a diagram describing an example of a method for applying a control parameter to a surgical instrument.
Figure 10B:
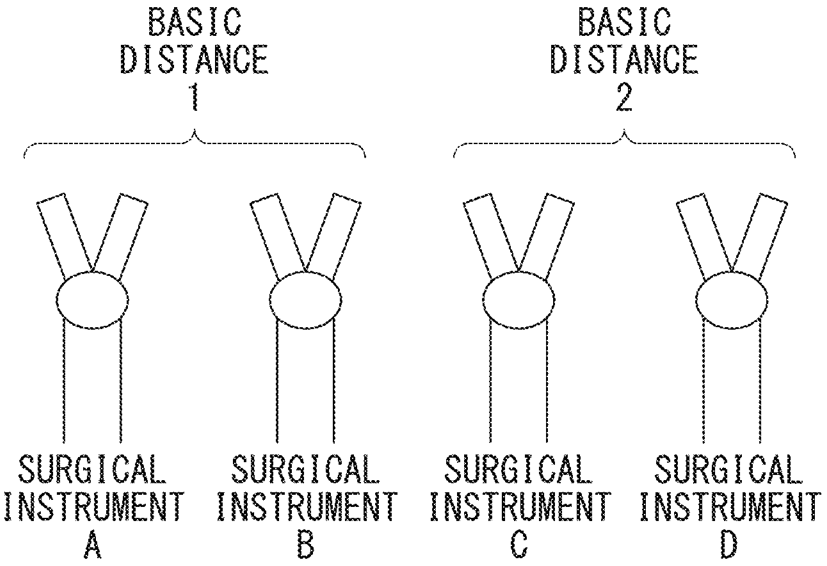
FIG. 10B is a diagram describing another example of the method for applying a control parameter to a surgical instrument.
Figure 10C:
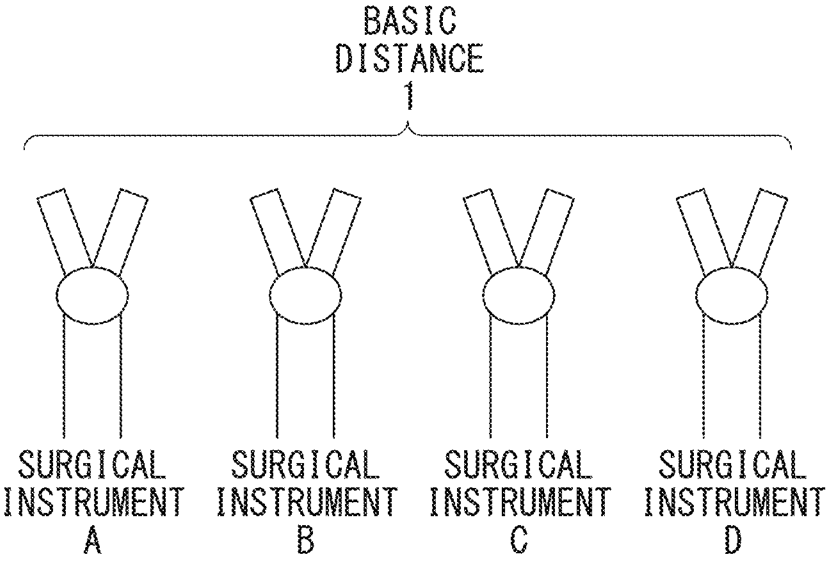
FIG. 10C is a diagram describing another example of the method for applying a control parameter to a surgical instrument.

FIGS. 10A to 10C describe the surgical instrument 20 to which the follow-up parameter P having been adjusted is applied. In FIG. 10A, the follow-up parameter P having been adjusted (for example, the basic distance) is applied to each type of the surgical instruments 20. In FIG. 10B, the follow-up parameter P having been adjusted is applied to each group of the surgical instruments 20. Each group includes, for example, the surgical instruments 20 of the same type or used by similar methods of use. In FIG. 10C, the follow-up parameter P having been adjusted is applied to all the types of the surgical instruments 20.

In addition, the follow-up parameter P having been adjusted may be applied to a target other than the surgical instrument 20. For example, the target may be an organ such as a blood vessel.

In each of the above-described embodiments, the storage unit 9 may store one or more pieces of the history data 14 in association with each item. For example, the storage unit 9 stores one or more pieces of the history data 14 on a surgery performed by a surgeon A in association with the surgeon A, and stores one or more pieces of the history data 14 on a surgery performed by a surgeon B in association with the surgeon B.

In this case, the processor 7 may calculate the recommended value of the control parameter 12 from at least one piece of the history data 14 for each item. For example, the processor 7 may calculate a recommended value for the surgeon A from the one or more pieces of the history data 14 associated with the surgeon A, and may calculate a recommended value for the surgeon B from the one or more pieces of the history data 14 associated with the surgeon B.

With this configuration, the follow-up parameter P suitable for each condition such as a surgeon, an operative method, a target organ, a facility, or a patient can be generated automatically.

It has been described in each of the above-described embodiments that the processor 7 searches for the subsidiary information corresponding to the surgery information at least in terms of the name of the surgeon. Instead of this, the processor 7 may search for the subsidiary information corresponding to the surgery information at least in terms of any one item. For example, in step SA2, the processor 7 may search for the subsidiary information corresponding to the surgery information in terms of the operative method or patient.

With this configuration, the control parameter 12 in accordance with various conditions of a surgery can be proposed to the surgeon. In this case, as described above, the processor 7 may propose the control parameter 12 calculated from one or more pieces of the history data 14 associated with each item.

It has been described in each of the above-described embodiments that the processor 7 calculates the recommended value from a piece of the history data 14. Instead of this, the recommended value may be calculated from a plurality of pieces of the history data 14.

An example of the plurality of pieces of the history data 14 is the history data 14 on a plurality of surgeries performed by the same surgeon. The plurality of surgeries may be a plurality of most recent surgeries performed by the same surgeon, or may be surgeries performed by the same surgeon in the same facility by the same operative method.

Another example of the plurality of pieces of the history data 14 is the history data 14 on an initial predetermined number of surgeries through use of the control unit 6. The predetermined number may be one or may be a plural number. In this case, the control parameter 12 initially set is used for the predetermined number of surgeries, and the recommended value of the control parameter 12 is calculated after the predetermined number of surgeries are carried out.

It has been described in each of the above-described embodiments that the processor 7 proposes, to the user, the control parameter 12 associated with the same surgeon as the surgeon in the surgery information. Instead of this, the control parameter 12 associated with a surgeon different from the surgeon in the surgery information may be proposed to the user.

For example, the processor 7 may propose the control parameter 12 calculated on the basis of the history data 14 on a surgery previously performed by a second surgeon as the control parameter 12 for a surgery to be performed now by a first surgeon. The first surgeon is the surgeon in the surgery information (that is, a surgeon who is going to perform a surgery now), and the second surgeon is a surgeon different from the first surgeon. With this configuration, the first surgeon can use, in the surgery, the appropriate control parameter 12 adjusted by the second surgeon without requiring labor.

The second surgeon may be a surgeon having more experience in surgeries than the first surgeon.

For example, the processor 7 may determine the second surgeon on the basis of the career (the number of surgeries) in the surgeon information. The second surgeon is an experienced surgeon who has experienced a larger number of surgeries than the first surgeon has.

With this configuration, the less-experienced first surgeon can use, in a surgery, the appropriate control parameter 12 adjusted by the experienced second surgeon in previous surgeries and reproduce, in the surgery of the first surgeon, the appropriate field of view F in the surgeries performed by the second surgeon.

The processor 7 may determine the second surgeon on the basis of another type of information other than the career.

In an example, the processor 7 determines the second surgeon on the basis of a facility to which he/she belongs. For example, the first surgeon is a surgeon in a branch hospital of a hospital, and the second surgeon is a surgeon in a main hospital of the hospital.

In another example, the processor 7 determines the second surgeon on the basis of a surgery region and a specialized field. For example, in a surgery of gallbladder, the first surgeon is a surgeon who specializes in large bowel but is going to be responsible for a laparoscopic cholecystectomy, and the second surgeon is a surgeon in general surgery.

In another example, the processor 7 determines the second surgeon on the basis of the patient information. For example, the second surgeon is a surgeon who has performed a larger number of surgeries of small female patients than the first surgeon has.

The processor 7 may calculate the recommended value of the control parameter 12 from the history data 14 on previous surgeries performed by a plurality of second surgeons. For example, the processor 7 may calculate the recommended value from the history data 14 associated with a plurality of second surgeons who have performed a large number of surgeries of small female patients.

In each of the above-described embodiments, the processor 7 may inquire of the user whether or not to change the control parameter 12 during a current surgery when a change in the control parameter 12 based on an operation of the user interface 4 satisfies a predetermined condition additionally after a surgery or instead of this.

With this configuration, the control parameter 12 can be changed to an appropriate value during the surgery, and the labor of the surgeon adjusting the control parameter 12 during the surgery can be reduced.

Figure 11A:
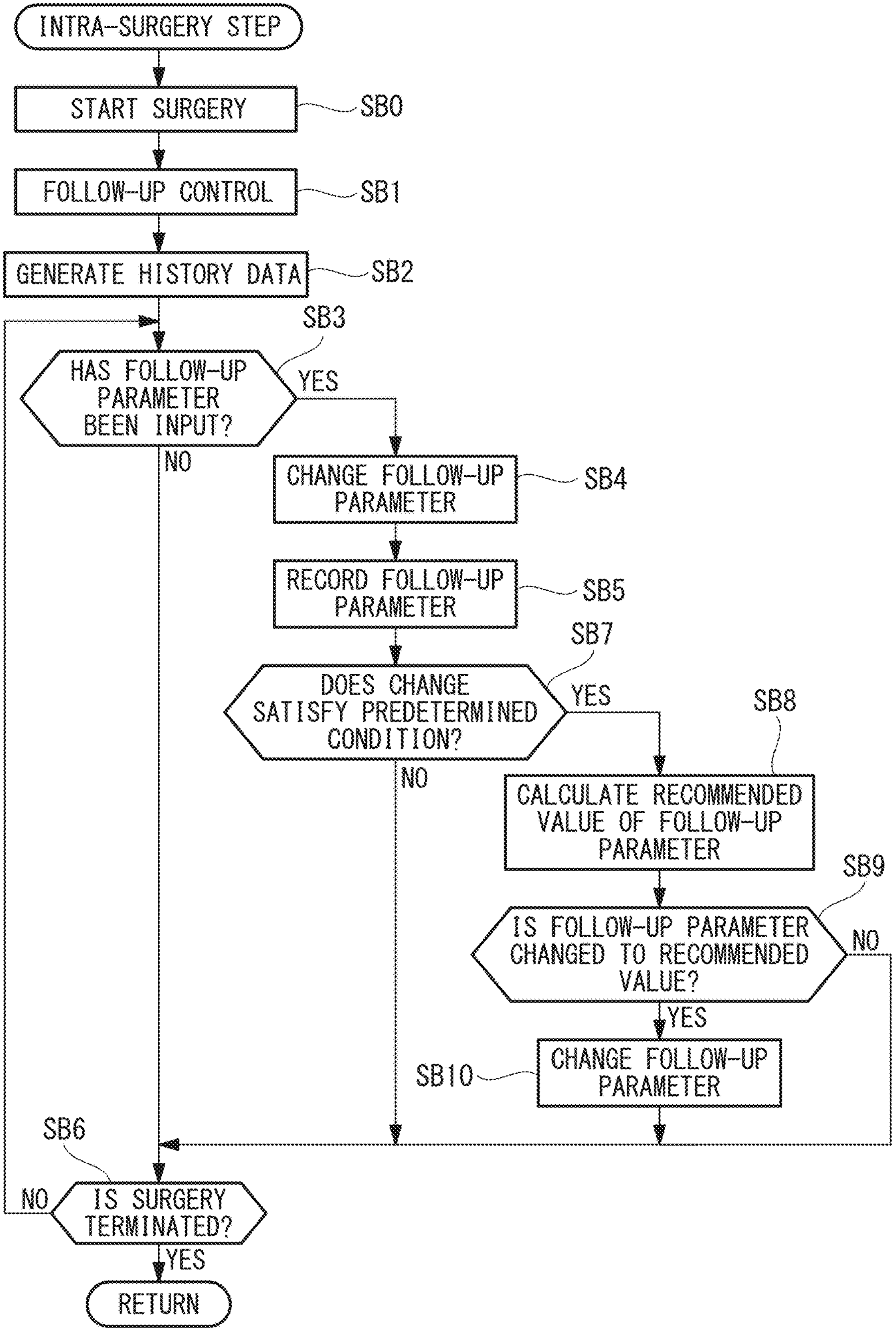
FIG. 11A is a flowchart of a modification of intra-surgery step SB of the first embodiment.

FIG. 11A illustrates a control method of a modification of the first embodiment. The predetermined condition is that the number of changes in the control parameter 12 based on operations of the user interface 4 becomes more than or equal to a predetermined number N.

In other words, when the number of changes in the follow-up parameter P reaches the predetermined number N (YES in step SB7), the processor 7 calculates the recommended value of the follow-up parameter P from the history data 14 on the current surgery having been recorded until then (step SB8) and inquires of the user whether or not to change the follow-up parameter P to the recommended value (step SB9). In a case where a response that the change is made is accepted (YES in step S9), the processor 7 changes the follow-up parameter P to the recommended value (step SB10).

The predetermined condition may be another condition.

Another example of the predetermined condition is that the follow-up parameter P is changed by more than or equal to the predetermined number N within a predetermined time period from the start of the surgery. In this case, it is possible to prevent a proposal for the change to the recommended value from being performed unnecessarily due to an increase in the number of changes in the latter half of the surgery.

Another example of the predetermined condition is that after a change in the follow-up parameter P, that follow-up parameter P is used continuously for more than or equal to a predetermined time period. A surgeon tends to continue using the appropriate follow-up parameter P for a long time period. Consequently, the follow-up parameter P which is appropriate for the surgeon can be determined on the basis of the long-time continuous use of the same follow-up parameter P.

Figure 11B:
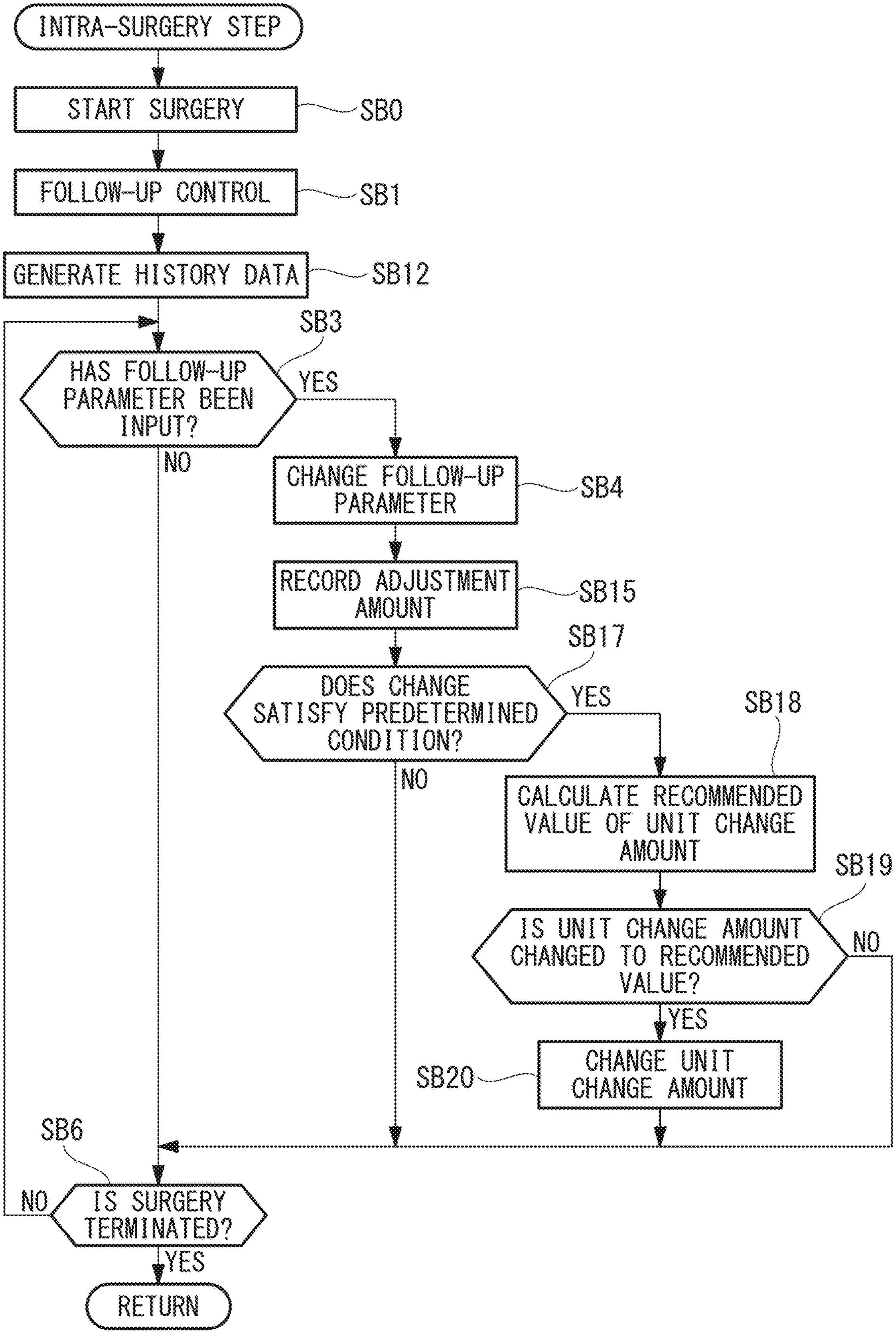
FIG. 11B is a flowchart of a modification of intra-surgery step SB of the second embodiment.

FIG. 11B illustrates a control method of a modification of the second embodiment. The predetermined condition is that the number of adjustments to the follow-up parameter P by the predetermined adjustment amount becomes more than or equal to the predetermined number N.

In other words, when the number of adjustments to the follow-up parameter P by the predetermined adjustment amount reaches the predetermined number N (YES in step SB17), the processor 7 calculates a recommended value of the unit change amount Δ from the history data 14 on the current surgery having been recorded until then (step SB18) and inquires of the user whether or not to change the unit change amount Δ to the recommended value (step SB19). In a case where a response that the change is made is accepted (YES in step SB19), the processor 7 changes the unit change amount Δ to the recommended value (step SB20).

The predetermined condition may be another condition.

Another example of the predetermined condition is that continuous operations of the user interface 4 are performed by more than or equal to the predetermined number N within a predetermined time period from the start of the surgery regardless of the adjustment amount.

Another example of the predetermined condition is that adjustments by the predetermined adjustment amount and an integral multiple of the predetermined adjustment amount are performed by more than or equal to the predetermined number N.

The present disclosure exerts an effect that enables an appropriate control parameter of a field of view to be obtained without requiring the labor of a surgeon.

Although embodiments of the present disclosure and modifications thereof have been described above, the present disclosure is not limited to these embodiments and can be modified as appropriate without departing from the scope of the present disclosure.

REFERENCE SIGNS LIST

1 endoscope system
2 endoscope
3 moving unit
4 user interface
6 control unit
7 processor
9 storage unit
11 control program
12 control parameter
13 subsidiary information
14 history data
20, 20A, 20B surgical instrument
B image
C specific region

The invention claimed is:

1. An endoscope system for controlling a field of view of an endoscope on a basis of a control parameter, the endoscope system comprising:

a storage configured to store history data on the control parameter during a surgery in association with subsidiary information on the surgery, the subsidiary information including information related to at least one of a surgeon, an operative method, or a patient of the surgery; and one or more processors comprising hardware, wherein the one or more processors are configured to calculate a recommended value of the control parameter on a basis of the history data, and wherein the history data is an operation log of a user interface for changing the control parameter.

2. The endoscope system according to claim 1, wherein control over the field of view of the endoscope is follow-up control of causing the endoscope to follow a follow-up target to continue capturing the follow-up target within a specific region in the field of view, and the control parameter is a follow-up parameter related to at least one of a positional relationship between the endoscope and the specific region or a follow-up speed of the endoscope for the follow-up target.

3. The endoscope system according to claim 1, wherein control over the field of view of the endoscope is follow-up control of causing the endoscope to follow a follow-up target to continue capturing the follow-up target within a specific region in the field of view, and the control parameter is a change amount obtained by operating the user interface for a follow-up parameter related to at least one of a positional relationship between the endoscope and the specific region or a follow-up speed of the endoscope for the follow-up target.

4. The endoscope system according to claim 3, wherein the change amount is a unit change amount of the follow-up parameter for each operation of the user interface.

5. The endoscope system according to claim 3, wherein the history data is a history of an adjustment amount of the follow-up parameter obtained by operating the user interface, and the adjustment amount is a change amount of the follow-up parameter within a predetermined time period.

6. The endoscope system according to claim 1, wherein the storage is configured to store one or more pieces of the history data in association with each item included in the subsidiary information, and the one or more processors are configured to calculate the recommended value from at least one piece of the history data for the each item.

7. The endoscope system according to claim 1, wherein the one or more processors are configured to:

receive surgery information related to at least one of a surgeon, an operative method, or a patient of an upcoming surgery, and set the recommended value calculated from the history data associated with the subsidiary information that matches the surgery information in at least one of the surgeon, the operative method, or the patient as the control parameter for the upcoming surgery.

8. The endoscope system according to claim 1, wherein the one or more processors are configured to:

inquire of a user whether or not to change the control parameter to the calculated recommended value, and in a case where a response to change is accepted, change the control parameter to the calculated recommended value.

9. The endoscope system according to claim 1, wherein the one or more processors are configured to automatically change the control parameter to the calculated recommended value.

10. The endoscope system according to claim 1, wherein, in a case where the control parameter is changed by a user more than or equal to a predetermined number of times during a current surgery, the one or more processors are configured to change the control parameter to the recommended value calculated on a basis of the history data of the current surgery.

11. The endoscope system according to claim 10, wherein, in a case where the control parameter is changed more than or equal to the predetermined number of times within a predetermined time period from a start of the surgery, the one or more processors are configured to change the control parameter to the recommended value.

12. The endoscope system according to claim 1, wherein the recommended value is an average, a median, a mode, a value used for a longest usage time, and a time-weighted average of the control parameter in the history data.

13. The endoscope system according to claim 1, further comprising an electric holder configured to change a position and an orientation of the endoscope, wherein the one or more processors are configured to control the electric holder on a basis of the recommended value.

14. The endoscope system according to claim 13, further comprising:

an endoscope configured to acquire an image; and a user interface configured to accept an operation by a user to change the control parameter.

15. A control method for controlling a field of view of an endoscope on a basis of a control parameter, the control method comprising:

causing a storage to store history data on the control parameter during a surgery in association with subsidiary information on the surgery, the subsidiary information including information related to at least one of a surgeon, an operative method, or a patient of the surgery; and calculating a recommended value of the control parameter on a basis of the history data, wherein the history data is an operation log of a user interface for changing the control parameter.

16. A non-transitory computer-readable recording medium storing a control program for causing a computer to execute a control method for controlling a field of view of an endoscope on the basis of a control parameter, the control method comprising:

causing a storage to store history data on the control parameter during a surgery in association with subsidiary information on the surgery, the subsidiary information including information related to at least one of a surgeon, an operative method, or a patient of the surgery; and calculating a recommended value of the control parameter on a basis of the history data, wherein the history data is an operation log of a user interface for changing the control parameter.

* * * * *